United States Patent [19]
Kobayashi et al.

[11] Patent Number: 5,810,620
[45] Date of Patent: Sep. 22, 1998

[54] ELECTRIC CONNECTOR PROVIDED WITH A SHIELDING PART FOR ELECTRICAL CONTACTS AT THE DISTAL END OF THE PLUG

[75] Inventors: Kazunari Kobayashi; Kenji Omachi; Yutaka Tatsuno, all of Hachioji; Masahiro Hagihara, Shirakawa; Atsushi Kidawara, Tachikawa; Tadayoshi Hara; Nobuyoshi Yazawa, both of Hachioji, all of Japan

[73] Assignee: Olympus Optical Co., Ltd., Tokyo, Japan

[21] Appl. No.: 863,077

[22] Filed: May 23, 1997

Related U.S. Application Data

[63] Continuation of Ser. No. 404,885, Mar. 16, 1995, abandoned, which is a continuation-in-part of Ser. No. 141,731, Oct. 27, 1993, Pat. No. 5,469,841.

[30] Foreign Application Priority Data

Oct. 29, 1992 [JP] Japan .................................... 4-291745
Feb. 24, 1993 [JP] Japan .................................... 5-035807
Feb. 24, 1993 [JP] Japan .................................... 5-035808

[51] Int. Cl.$^6$ .................................................... H01R 23/10
[52] U.S. Cl. ........................... 439/610; 439/60; 439/609; 439/271; 439/198; 439/347; 439/951; 392/379
[58] Field of Search .............................. 439/60, 77, 493, 439/497, 607, 608, 610, 660, 668, 76.1, 271, 609, 347, 206, 198, 951; 219/209; 392/379

[56] References Cited

U.S. PATENT DOCUMENTS 3,205,471 9/1965 Herrmann .................................. 439/631
3,329,925 7/1967 Johnson et al. .......................... 439/610
3,334,325 8/1967 Conrad et al. ............................. 439/60

(List continued on next page.)

FOREIGN PATENT DOCUMENTS 44-28832 11/1969 Japan .
58-4278 1/1983 Japan .
60-207111 10/1985 Japan .
60-184501 12/1985 Japan .
2-266314 10/1990 Japan .

OTHER PUBLICATIONS

IBM Technical Disclosure, Jones, vol.20, No. 11A, p. 4315, Apr. 1978.
IBM Technical Disclosure, vol. 11, No. 7, p. 723, Dec. 1968.
Research Disclosure, Kenneth Mason Publications, England, #28018, Aug. 1987.

*Primary Examiner*—Neil Abrams
*Attorney, Agent, or Firm*—Armstrong, Westerman, Hattori, McLeland, and Naughton

[57] ABSTRACT

An electrical connector having an electrical plug (102) to be plugged into an electrical receptacle (130). The electrical plug (102) includes an electrically insulative plate-like substrate and a plurality of first electrical contacts (118) formed in parallel on at least a side surface at one end of the substrate for a predetermined length from the one end. The plug further includes a shielding part (126) formed of an electrical conductor which substantially shields all of the substrate in a position nearer an end other than the one end having the electrical contacts (118). The electrical receptacle includes an electrically insulative receiving member (138) forming at least part of a recess in which the substrate of the plug is inserted. A plurality of second electrical contacts (142) are arranged in the receiving member (138) so as to contact the plurality of contacts in the plug whenever the substrate of the plug is inserted into the recess. The electrical receptacle (130) also includes a shielding electrical contact (140) formed to contact the shielding part of the electrical plug (102). The shielding electrical contact includes a liquid removing member (235) for removing liquid from the substrate during insertion into the recess. A heated air mechanism (271, 273) may be included to assist in liquid removal. The shielding may also serve the purpose of latching the plug and receptacle together and the plug may be of circular shape.

22 Claims, 19 Drawing Sheets

U.S. PATENT DOCUMENTS

| | | | |
|---|---|---|---|
| 3,740,698 | 6/1973 | Jerominek | 439/493 |
| 3,803,533 | 4/1974 | Taplin | 439/328 |
| 3,824,529 | 7/1974 | Dorrell | 439/418 |
| 3,906,953 | 9/1975 | Wallace et al. | |
| 4,129,349 | 12/1978 | Von Roesgen | 439/49 |
| 4,325,606 | 4/1982 | Ikuno et al. | |
| 4,544,227 | 10/1985 | Hirose | 439/607 |
| 4,611,872 | 9/1986 | Ito et al. | 439/277 |
| 4,851,866 | 7/1989 | Ciarlei et al. | 354/62 |
| 4,863,304 | 9/1989 | Bauer et al. | 403/37 |
| 4,871,319 | 10/1989 | Babow | 439/493 |
| 4,892,706 | 1/1990 | Kralovic et al. | 422/28 |
| 5,035,631 | 7/1991 | Piorunneck et al. | 439/630 |
| 5,122,065 | 6/1992 | Dudek et al. | 439/76.1 |
| 5,188,094 | 2/1993 | Adair . | |
| 5,234,357 | 8/1993 | Yamaguchi | 439/354 |
| 5,295,867 | 3/1994 | Bethurum | 439/607 |
| 5,326,282 | 7/1994 | Igarashi et al. | 439/607 |

ELECTRIC CONNECTOR PROVIDED WITH A SHIELDING PART FOR ELECTRICAL CONTACTS AT THE DISTAL END OF THE PLUG

This application is a continuation of application Ser. No. 08/404,885, filed Mar. 16, 1995, now abandoned, which is a Continuation-in-Part of application Ser. No. 08/141,731 filed Oct. 27, 1993, now U.S. Pat. No. 5,469,841.

BACKGROUND OF THE INVENTION

1. Field of the Invention

The present invention relates to an electrical connector which electrically connects an electrical plug when inserted into an electrical receptacle and which is provided with a shielding part near the proximal end for electrical contacts at the distal end in the electrical plug.

2. Description of the Related Art

A prior art example of an electrical connector is disclosed, for example, in the publication of Japanese patent application publication No. 28832/1969. Because this kind of electrical connector is used in various fields, the need for electromagnetic shielding of the periphery of an electrical connector will often occur.

In such a case, as disclosed, for example, in the publications of Japanese patent applications laid open Nos. 266314/1990 and 4278/1983, it is generally known to electromagnetically shield an electrical connector by converting at least one of a plug and receptacle with a metallic tube.

However, in the method disclosed in the publication of Japanese patent application laid open No. 266314/1990, a small contact piece is fitted to the plug side and it is impossible to electromagnetically shield all the periphery of the electrical connector.

Also, according to the method disclosed in the publication of Japanese patent application laid open No. 4278/1983, an electromagnetic shielding member separate from the electrical connector must be provided for each of the plug and receptacle. The electrical connector must have a structure allowing contact of these electromagnetic shielding members with each other, therefore the structure will be complicated and the cost will be high.

The plug extensively used for an ear phone or the like has a structure in which two or three ring-shaped contacts are separately formed in the axial direction of the plug, has a simple structure and has a shielding function.

However, this plug cannot be substantially applied to an electrical instrument requiring many electrical contacts, because it has the following defects.

That is to say, in the case where the plug is inserted into the receptacle or in the case where the plug is removed from the fitted state, the electrical contacts on the distal side will electrically contact the receiving contacts other than the corresponding receiving contacts on the receptacle side, the number of contacts will increase and various connected states will be generated.

In the case where electrical contacts on the plug side conduct merely with grounded contacts, there will be few problems but, in the case where they conduct with electrical contacts other than grounded contacts, for example, such devices will likely be destroyed when an electrical current flows. That is to say, the contacts on the plug side will conduct with contacts other than the grounded contacts with which the contacts on the plug side should not conduct while they are inserted or removed. In the case where the power source is off, there will be generally no problem but, in the case where the power source is on, there will be the same state as the mis-connected state. Therefore, the use of the electrical contacts on the plug side will be limited to only the electrical instruments which will not fail even in the case of such mis-connection. In case they are applied to general electrical instruments, the possibility of a failure occurring when the plug is fitted or removed will be so high that they will not be able to be applied.

SUMMARY OF THE INVENTION

An object of the present invention is to provide an electrical connector which is low in the number of component parts, has a simple structure and is yet provided with sufficient electromagnetic shielding function.

Another object of the present invention is to provide an electrical connector which can be applied to many electrical instruments and has wide applicability.

The electrical connector of the present invention comprises:

an electrical plug having:
   an insulating member having an electrically insulating property;
   a plurality of first electrical contacts which are respectively formed in parallel on the surface of the insulating member as exposed on the surface for a predetermined length from one end side toward the other end side; and
   a shielding part formed of an electrical conductor to shield substantially all the range of the surface nearer to the other end than to the part in which a plurality of first electrical contacts are formed; and
an electrical receptacle having:
   a receiving member forming at least a part of a recess in which the insulating member is inserted on one end side and having an electrically insulating property;
   a plurality of electrical contacts arranged so as to be formed in the receiving member and to contact respectively with the plurality of first electrical contacts in the case where the insulating member is inserted on one side into the recess; and
   a shielding electrical contact formed in a position of contact with the shielding part,
so that, when the electrical plug is fitted to the electrical receptacle, the shielding part and shielding electrical contact will be positioned outside the first and second electrical contacts and the inner first and second electrical contacts will be able to be shielded, as the plurality of first electrical contacts are formed in parallel with the inserting direction on the other end side from the one end of the insulating member, in the case where the plug is fitted or removed, the respective first electrical contacts will be fitted to or removed from the respective corresponding second electrical contacts and the generation of mis-connection will be able to be dissolved and, therefore, the electrical connector of the present invention can be extensively applied as an electrical connector to be used to connect electrical instruments.

BRIEF DESCRIPTION OF THE DRAWINGS

FIGS. 1 to 7B relate to the first embodiment of the present invention.

FIG. 1 is a general formation view of an endoscope apparatus provided with a modification of the first embodiment.

FIG. 2 is a formation view showing a structure of the formation in FIG. 1.

FIG. 4A is an explanatory view showing a dry processed state wherein an electrical plug is connected to an opening part. FIG. 4B is an explanatory view showing a state after the dry process wherein the electrical plug is fitted to the electrical receptacle.

FIG. 5 is a general formation view of an endoscope apparatus provided with an electrical connector of the first embodiment.

FIGS. 7A and 7B are sectioned views showing the structure of an electrical receptacle respectively before and when the electrical plug is connected.

FIG. 11 is a perspective view showing a plug in the electrical connector in the fourth embodiment.

FIG. 12 is a plan view showing the first layer of the printed wiring board shown in FIG. 11.

FIG. 13 is a plan view showing the second layer of the printed wiring board shown in FIG. 11.

FIG. 14 is a bottom view showing the third layer of the printed wiring board shown in FIG. 11.

FIG. 15 is a plan view showing the arrangement of the electromagnetically shielding contact members and the electrical contacts.

FIG. 16 is a sectioned view when the plug shown in FIG. 11 is inserted into the receptacle.

FIG. 20A is a side view of the printed wiring board in the fourth embodiment for the comparison with the electrical connector in the sixth embodiment.

FIG. 20B is a side view showing a printed wiring board of the electrical connector in the fifth embodiment.

FIG. 23A is a perspective view of the same.

FIG. 23B is a side view of the same.

FIG. 24A is a perspective view of the same.

FIG. 24B is a side view of the same.

DESCRIPTION OF THE PREFERRED EMBODIMENTS

Prior to explaining the first embodiment, the formation of an endoscope apparatus 1 provided with a modification of the first embodiment shall be explained.

Figure 1:
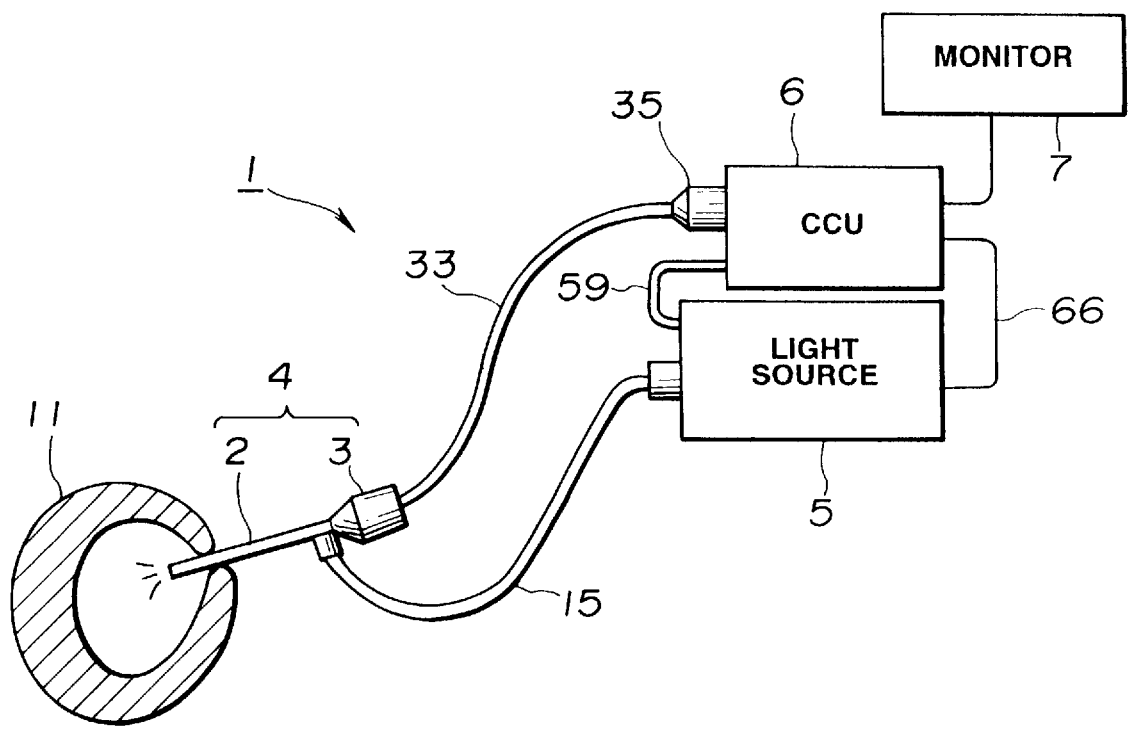

As shown in FIG. 1, the endoscope apparatus 1 provided with the modification of the first embodiment comprises an endoscope 4 of a TV camera outside fitted system (as a device to be inserted into an organism) comprising a rigid endoscope 2 having an elongate rigid inserted section 8 and a TV camera 3 fitted to the ocular part 10 of this rigid endoscope 2, a light source apparatus 5 feeding an illuminating light to the rigid endoscope 2, a camera controlling unit (which shall be abbreviated as a CCU hereinafter) 6 processing the signal for the TV camera 3 and a color monitor 7 displaying the video signal output from this CCU 6.

Figure 2:
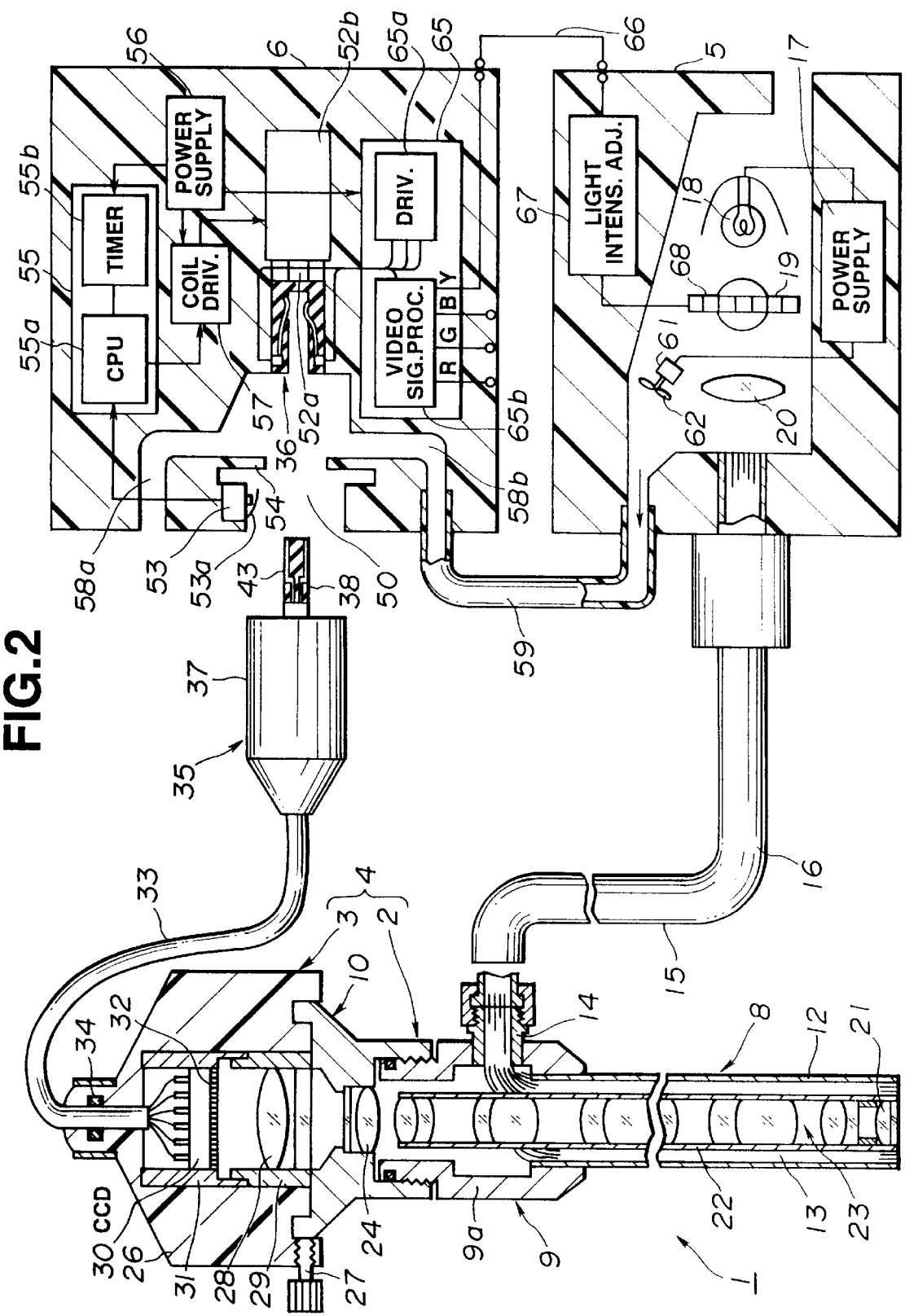

As shown in FIG. 2, the rigid endoscope 2 comprises an elongate rigid inserted section 8 formed of a metallic cylindrical pipe 12, a gripped section 9 large in the diameter at the proximal end of this inserted section 8 to be gripped and a conical ocular section 10 provided at the rear end of this gripped section 9. The inserted section 8 is inserted into a body to be examined 11 through a small hole or the like formed in the abdominal part or the like of the body to be examined as an organism.

A light guide 13 formed of a fiber bundle transmitting an illuminating light is inserted through a cylindrical jacket pipe 12 forming the inserted section 8. This light guide 13 leads at the rear end to a light guide mouthpiece 14 bent at the gripped section 9.

This mouthpiece 14 is pressed into an opening provided on the side of the frame 9a of the gripped section 9 fixed to the frame 9a by brazing or the like to be of a liquid-tight and moisture-proof structure so that neither liquid nor moisture may enter the opening.

A light guide cable 15 having a flexibility is connected at one end to this light guide mouthpiece 14. A light guide connector 16 provided at the other end of this cable 15 can be removably fitted to the light source apparatus 5. A lamp 18 lighted by electric power fed from a power source 17 is contained within the light source apparatus 5. The illuminating light of this lamp 18 is radiated to the end surface of the light guide connector 16 through a diaphragm 19 and condenser lens 20.

The illuminating light radiated to this end surface is transmitted by the light guide within the light guide cable 15 and is fed to the light guide 13 within the rigid endoscope 2 from the light guide mouthpiece 14. The illuminating light transmitted by this light guide 13 is projected forward from the distal surface fixed to an illuminating window at the distal part of the inserted section 8 to illuminate the affected part or the like within the examined body 11.

The optical image of the position of the illuminated affected part or the like is formed on the focal plane by an objective lens 21 fitted to an observing window provided at the distal part of the inserted section 8. This objective lens 21 is fitted near the distal end of a lens containing tube 22 arranged concentrically within the jacket pipe 12. A cover glass is fitted in front of this objective lens 21 to make the observing window liquid-tight and gas-tight. Also, the illuminating window is fitted with the light guide 13 with a bonding agent or the like so as to be water-proof and air-tight.

The optical image by the objective lens 21 is contained in the lens containing tube 22 and is transmitted rearward by an image guide formed of a relay optical system 23 arranged on the optical axis of the objective lens 21. The relay optical system 23 is arranged within the inserted section 8 and gripped section 9. An ocular lens 24 is arranged within the ocular section 10 as opposed to the rear end of the relay optical system 23. This ocular section 10 is connected to the frame 9a of the gripped section 9 through a screwed mechanism.

A sealing O-ring is interposed in this connecting part so as to form a water-proof structure which allows no liquid to enter through the connecting part and a moisture-proof structure into which no water vapor will enter.

Also, the ocular section 10 and the ocular window of the ocular section 10 are closed with cover glasses so as to be liquid-tight to prevent liquid from entering the interior and to be moisture-proof to prevent water vapor from entering the interior.

The optical image transmitted by the relay optical system 23 can be magnified and observed from the ocular window through the ocular lens 24.

As explained above, the rigid endoscope 2 is liquid-tight and moisture-proof and can be dipped in chemicals to be sterilized and also dipped in a detergent liquid to be washed.

The head frame 26 of the TV camera 3 is removably fitted to the ocular section 10, for example, by a fixing screw 27. An image forming lens 28 is fixed through a lens frame 26 to an opening opposed to the ocular window in this head frame 26. This opening is closed by a cover glass, is liquid-tight so that no liquid may enter the interior and is moisture-proof so that no water vapor may enter the interior.

A CCD frame 31 fitted with a charge coupled device (hereinafter "CCD") 30 as an electrical device is connected to the lens frame 29 at the rear end and is fixed with a screw or the like (not illustrated). The optical image transmitted by the relay optical system 23 is imaged on the image taking surface (photoelectric converting surface) of the CCD 30 through the ocular lens 24 and image forming lens 28. A color separating filter 32 is fitted to this image taking surface of the CCD 30 so that an optical image having colors separated, for example, into R, G and B in each pixel may be formed on the image taking surface of the CCD 30.

A plurality of signal wires of a signal transmitting cable 33 are connected by soldering or the like to a plurality of leads projecting on the back surface of the CCD 30. This signal transmitting cable 33 is extended outward through a hole in the head frame 26. A sealing O-ring 34 is interposed in this hole and is fitted by caulking or the like to a projection at the rear end of the head frame 26 so that an energizing force may act to press the O-ring 34 and the structure may be made liquid-tight to prevent a liquid from entering the hole and moisture-proof to prevent the entrance of water vapor.

An electrical plug 35 in the modification of the first embodiment is fitted to the distal end of the outward extended signal transmitting cable 33 and can be removably fitted to an electrical receptacle 36 of the CCU 6.

Figure 3A:
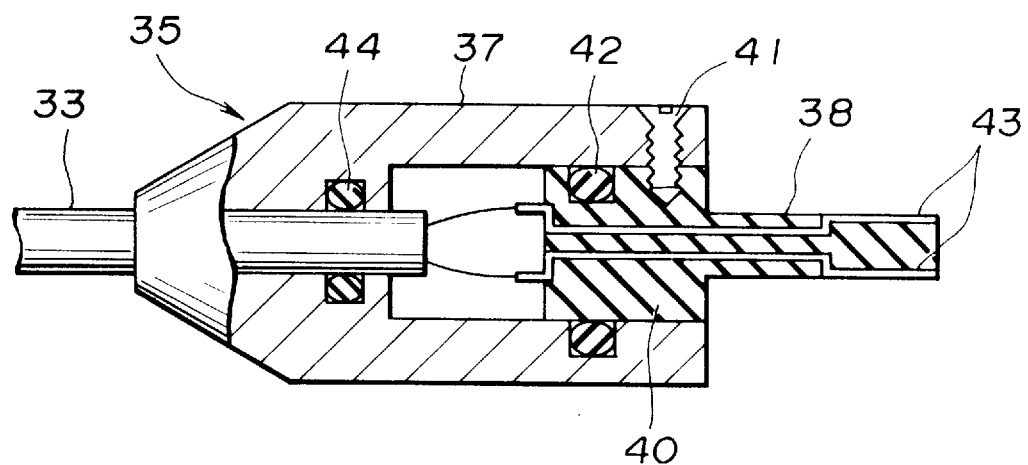
FIGS. 3A and 3B are respectively a sectioned side view and a plan view.
Figure 3B:
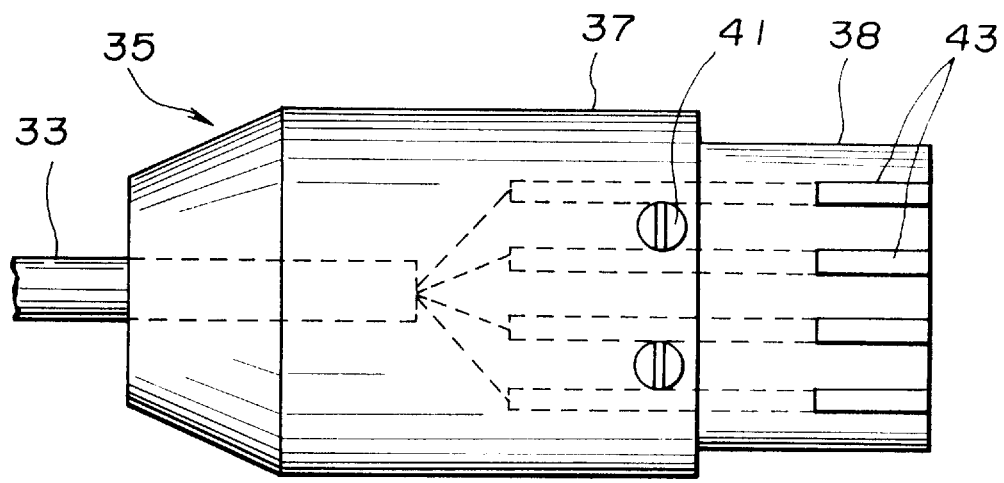

As shown in FIGS. 3A and 3B, this electrical plug 35 is a card edge type wherein a card (lamina)-like plug part 38 projects from the distal end of the plug body 37. In this plug part 38, a thick proximal part 40 is fitted in a recess in the plug body 37 made of a metal and is fixed by a fixing screw 41. A sealing O-ring 42 is interposed in the part fitted to the plug body 37 so as to make the structure liquid-tight and moisture-proof.

A plurality of electrical contacts 43 are embedded within the plug part 38 formed of an insulator and are exposed on the distal end side to be flush with both surfaces (both surfaces above and below in FIG. 3A) of the card of the plug part 38. The rear ends of the respective electrical contacts 43 are exposed in the rear of the proximal end part 40, are passed through a hole in the plug body 37 and are connected by soldering with respective signal lines pulled out of the distal end of the signal cable 33 contained within the recess.

Also, a sealing O-ring 44 is interposed in the hole in the plug body 37 to make the structure liquid-tight and moisture-proof.

As explained above, the TV camera 3 fitted in the ocular section 10 of the rigid endoscope 2 is also made water-tight and moisture-proof in the structure and can be dipped in chemicals to be sterilized and in a detergent liquid to be washed.

The structure of the CCU 6 wherein the electrical plug 35 at the distal end of the signal transmitting cable 33 of the TV camera 3 is removably fitted shall be explained as follows.

A drying and removing mechanism 51 for drying and removing the moisture deposited on the electrical plug 35 is provided within an opening 50 provided on the front surface of the CCU 6. An electrical receptacle 36 as fitted to a plunger 52a is arranged in the depth of this opening 50. After the moisture is removed by the drying and removing mechanism 51, the electrical plug 35 is connected with the electrical receptacle 36 moved forward by the movement of the plunger 52.

Figure 4A:
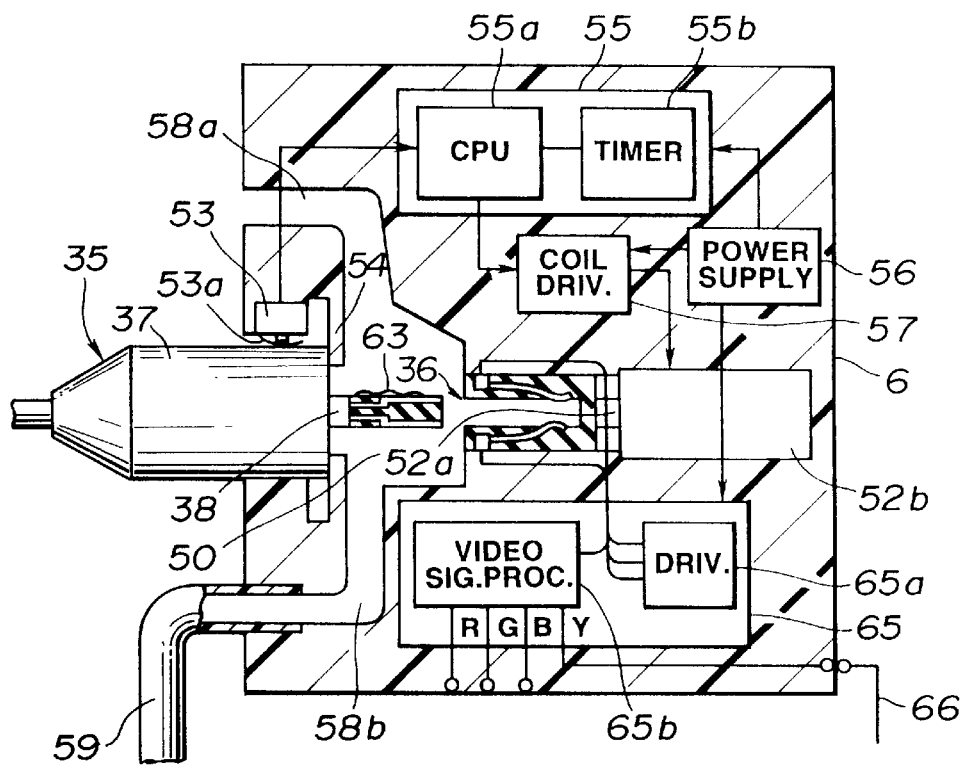
FIGS. 4A and 4B show a CCU.
Figure 4B:
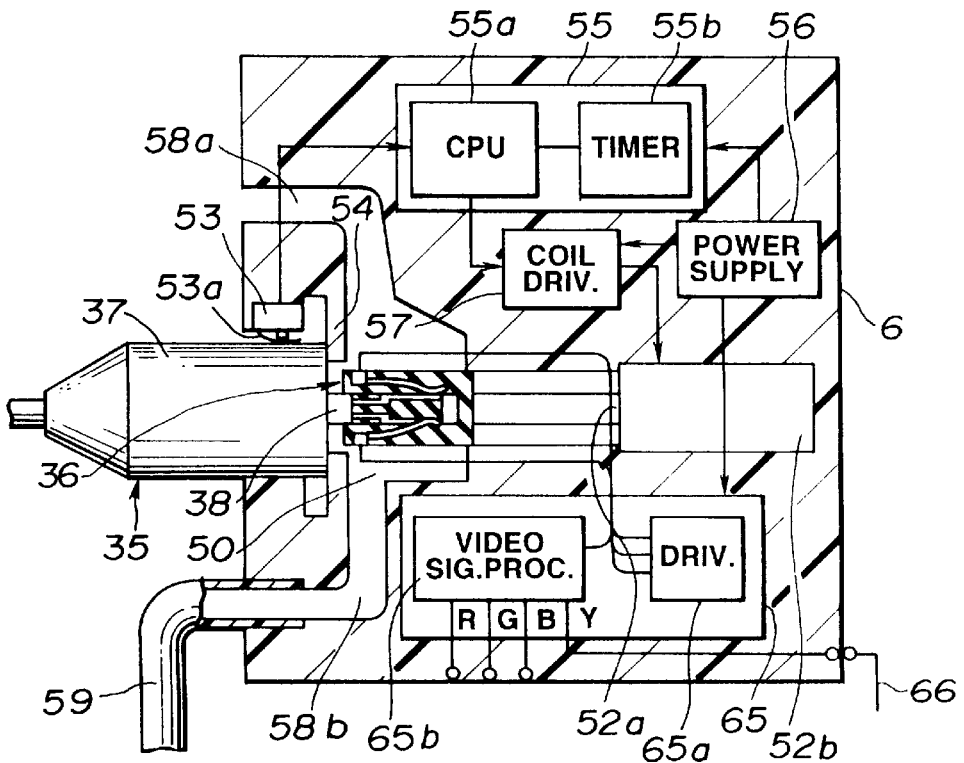

This electrical receptacle 36 has a plurality of contacts 36c embedded in an insulator 36b provided with an opening 36a fitting to the plug part 38 may be exposed on the opening 36a side. When the plug part 38 is contained in the opening 36a as shown in FIG. 4B, the respective electrical contacts 43 of the plug part 38 will conduct with the electrical contacts 36c of the electrical receptacle 36.

The shape of the vicinity of the inlet of the opening 50 is made such that the electrical plug 35 may be inserted. For example, a switch lever 53a of a microswitch 53 is provided to project inside the opening 50 on the inside wall surface near the inlet of the opening 50. When the electrical plug 35 is inserted as shown in FIG. 4A, the switch lever 53a will be pressed on the outer surface of the plug body 37 of the electrical plug 35 and the microswitch 53 will be on.

A projection 54 is provided in a position adjacent to the microswitch 53 within the opening 50 and on the side opposed to this position so that the front surface of the plug body 37 of the inserted electrical plug 35 may contact the respective projections 54 and the position may be regulated.

The microswitch 53 is connected with a CPU 55a forming a controlling circuit 55. When the microswitch 53 is on, after the set time set by a timer 55b, the CPU 55a will control the current to be fed to an electromagnetic coil 52b through a coil driver 57 from a power source 56, the plunger 52a will be projected by the electromagnetic coil 52b (against a spring not illustrated) and the electrical receptacle 36 will be moved forward and will be fitted to the electrical plug 35.

An air exhausting path 58a and air feeding path 58b are provided, for example, on the upper and lower wall surfaces within the opening 50. The air feeding path 58b is connected with the light source apparatus 25 through an air feeding tube 59. A fan 62 rotated and driven by a motor 61 is arranged, for example, in the upper position of the lens 20 within the light source apparatus 25 and heat generated by the lamp 18 or the like is exhausted through the tube 59 from the opening. The air (mentioned as heated air) containing this exhausted heat is fed into the CCU 6 and is utilized to remove a liquid from the electrical plug 35.

When the heated air is blown to the plug part 38 from the lower side opposed to the plug part 38 as shown in FIG. 4A and, even if the moisture 63 of the washing liquid remains, for example, on the surface of the plug part 38, the remaining moisture will be evaporated by the heated air and will be exhausted out through the air exhausting path 58a. Therefore, some time after the electrical plug 35 is fitted to the opening 50, the moisture 63 will be removed and the plug part 38 will be dry.

After the time required for sufficient drying, the time set by a timer 55a will elapse. This elapsed time is transmitted to the CPU 55 which makes the current flow to the electromagnetic coil 52b through the coil driver 57. Then, the plunger 52a formed of an electromagnet will be moved forward together with the electrical receptacle 36 fitted at the distal end by the magnetic repulsion or the like.

The electrical receptacle 36 is connected with the electrical plug 35 as shown in FIG. 4B, the respective electrical contacts 43 of the electrical plug 35 contact with the respective electrical contacts 36 of the electrical receptacle 36 to electrically conduct.

In FIG. 2, the respective electrical contacts of the electrical receptacle 36 are connected to the CCD driving circuit 65a and video signal processing circuit 65b forming the signal processing circuit 65. In the case where the electrical plug 35 is connected to the electrical receptacle 36, a driving signal will be applied to the CCD 30 from the CCD driving circuit 65a and a CCD output signal photoelectrically converted by the CCD 30 will be put into the video signal processing circuit 65b. The CCD output signal is processed by this video signal processing circuit 65b. Three primary color signals of R, G and B are produced as standard video signals and are put out to the color monitor 7.

Also, the video signal processing circuit 65b produces a luminance signal Y which is put into a light amount adjusting circuit 67 of the photoelectric apparatus 5 through a cable 66.

In this light amount adjusting circuit 67, the luminance signal Y is integrated, for example, for one frame period to produce an integrated signal. This integrated signal is compared with a reference potential corresponding to a reference brightness. An error signal from the reference potential is produced and is applied to a motor 68 through the driving circuit. The rotation angle of the diaphragm 19 is controlled to control the passage of the illuminating light amount to properly control the illuminating light.

For example, when the level of the luminance signal Y is too high, the motor 68 will be rotated by the error signal in the direction in which the light amount passed through the diaphragm 19 becomes small and a proper illuminating light amount will be set. On the contrary, when the level of the luminance signal Y is too low, the motor 68 will be rotated by the error signal in the direction in which the light amount passed through the diaphragm 19 becomes large and a proper illuminating light amount will be set. In FIG. 3, the diaphragm 29 is formed by laminating small hexagonal rings and is open to pass the illuminating light without substantially intercepting it. When the motor is rotated from this state to incline the diaphragm, the light will be intercepted by the wall surfaces of the hexagonal rings and the passed light amount will decrease.

That is to say, in this embodiment, after the plug part 38 has dried, the electrical plug 35 will be connected to the electrical receptacle 36. Therefore, even if the plug part 38 wet with moisture 63 (See FIG. 4A) on the surface is connected to the opening 50, after the moisture 63 is removed, the plug part 38 will be connected to the opening 36a of the electrical receptacle 36. Therefore, even when the current is fed to the electrical receptacle 36 side, any possible short-circuit caused by an excess current or the like flowing through the short-circuited electric contact 43s due to the moisture 63 will be able to be prevented.

In the modification of the first embodiment, there is formed a liquid removing mechanism in which liquid is removed by utilizing heat of a heat radiating mechanism radiating heat generated by the light source apparatus 5.

Figure 5:
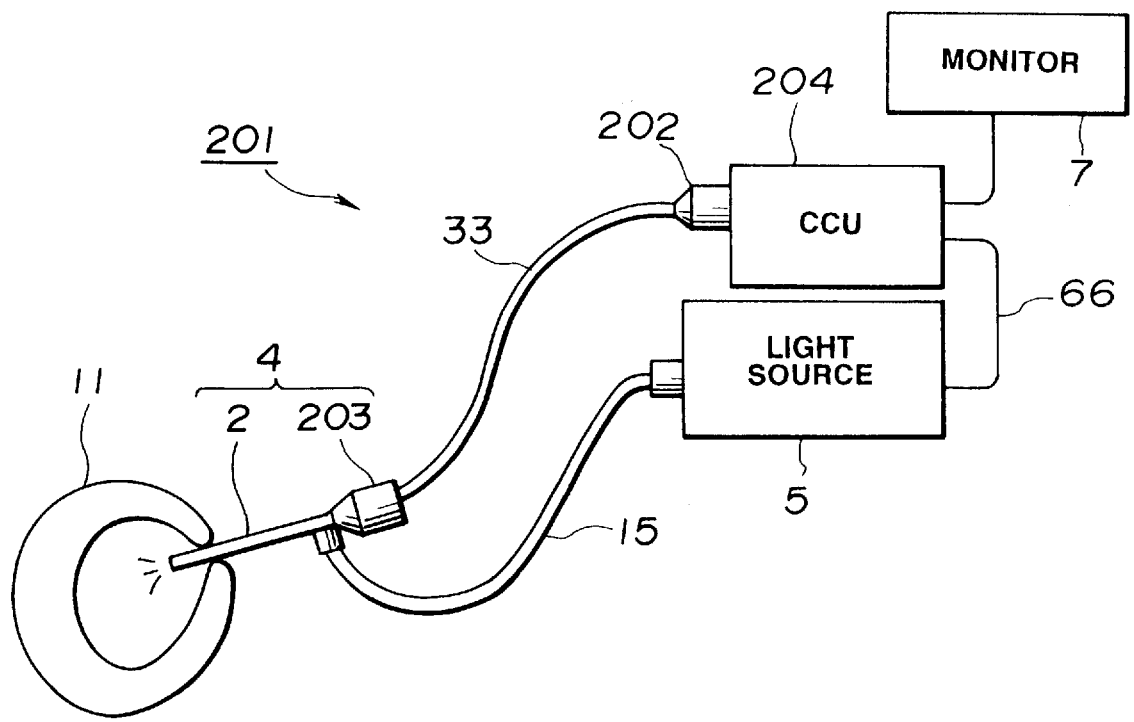

FIG. 5 shows an endoscope apparatus 201 provided with the first embodiment of the present invention. This endoscope apparatus 201 has a TV camera 203 having an electrical plug 202 different from the electrical plug 35 of the modification and a CCU 204 having a drying processing means different from that of the CCU 6. The others are of the same formations as of the modification.

Figure 6A:
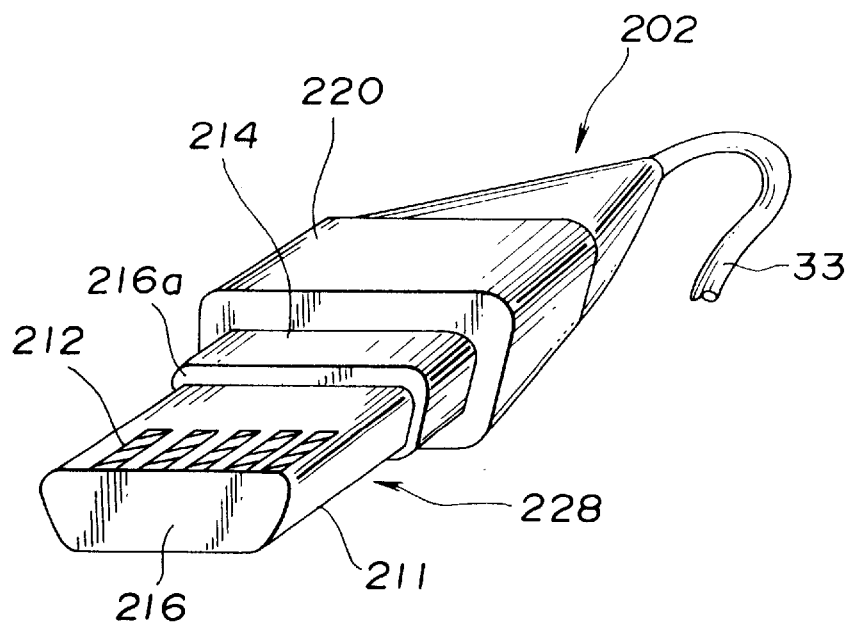
FIGS. 6A and 6B are perspective views showing respectively the contour and internal structure of an electrical plug.
Figure 6B:
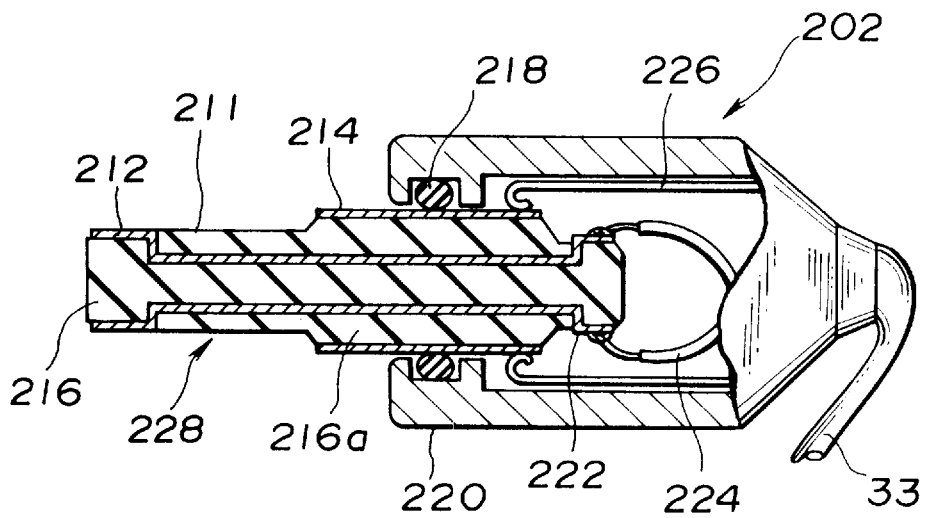

FIGS. 6A and 6B show the structure of the electrical plug 202. The electrical plug 202 provided at the distal end of the cable 33 of the TV camera 202 has a base 211 provided with a plurality of plane-like contact patterns (electrical contacts) 212 and 222 on both surfaces of a plate-like insulating member 216. An electrical plug body 228 is formed by providing a plane shield pattern 214 which is a contact of an electrical plug side shielding part for intercepting noise on the outer periphery of the base 211.

The electrical plug 202 forming the electrical connector of the first embodiment is formed by liquid-tightly connecting this electrical plug body 228 with an electrical plug cover 220 through a sealing member 218.

The insulating member 216 has a flat shape. A plurality of contact patterns 212 are formed at the tip of the base 211 having the flat plane. When these contact patterns 212 contact with electrical contacts provided in an electrical receptacle (See FIGS. 7A and 7B) on the CCU 204 side, the CCU 204 and TV camera 203 will be electrically connected with one another.

Also, contact patterns 222 are formed in the same manner also at the rear end of the base 211. The contact patterns 212 and 222 conduct to correspond to each other through the interior of the insulating member 216.

The insulating member 216 is made a flat thick part 216a having elevated flat planes in the intermediate parts of the contact patterns 212 and 222. A shielding pattern 214 having a very smooth plane over the entire periphery of the surface of this thick part 216a is provided with a conducting member such as a copper foil.

The electrical plug cover 220 and electrical plug body 228 are connected with each other to be liquid-tight, with the surface of this shielding pattern 214 as a sealing surface. That is to say, the electrical plug body 228 and electrical plug cover 220 are made liquid-tight by interposing a sealing member 218 between the surface of the shielding pattern 214 and the inside surface of the tip part of the electrical plug cover 220.

In this structure, the rear end side positions of the contact pattern 222 and shielding pattern 214 are arranged within the electrical plug cover 220. Various signal lines 224 which lead into the electrical plug cover 220 through a cable 33 are soldered to the contact pattern 222 positioned within the electrical plug cover 220. A shielding member 226 is led at the tip into the interior of the electrical plug cover 220 through the cable 33. The shielding member 226 covers the various signal lines 224 of the cable 33 with cable shielding lines connected with this shielding member 226 and shields them by grounding.

The shielding member 226 forms the shielding pattern 214 and the electrical plug side shielding part by contacting at the tip with the rear end side of the shielding pattern 214 positioned in the interior of the electrical plug cover 220. In this case, when the contacts of the CCU 204 side shielding part are in perfect contact with the shielding pattern 214 by fitting the electrical plug 202 with the electrical receptacle of the CCU 204, outside noises will be intercepted and the noises from outside the fitted camera 203 side to the CCU 204 side will be able to be controlled.

Therefore, in the endoscope apparatus 201 of such formation, as the liquid-tight structure of the electrical plug 202 is formed by making the surface of the shielding pattern 214 forming a very smooth plane over the entire periphery a sealing surface, a highly reliable liquid-tight sealing surface can be obtained.

As the electrical plug body including the sealing surface is not formed by molding but the shielding pattern 214 as a sealing surface is formed on the outer surface of the base 211 made of the insulating member 216, the production yield will be high and the plug part will be able to be easily repaired. Further, because the electrical contact patterns 212 are provided in plane form in the base 211 having a flat surface, if a liquid is deposited on the base 211, it will be easily wiped off; therefore, the electrical contacts will be able to be prevented from short-circuiting.

Figure 7A:
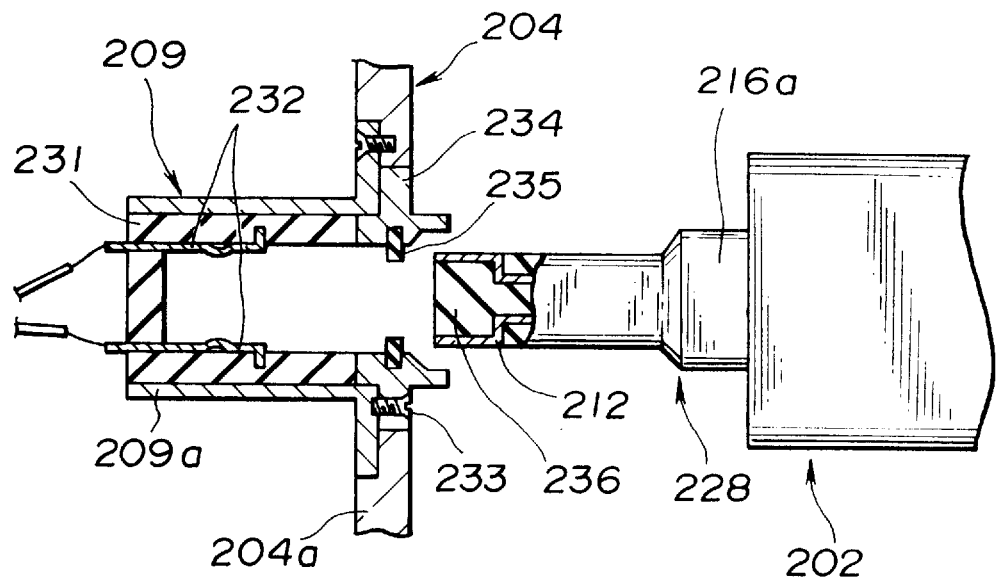

FIG. 7A shows a structure around the receptacle 209 in the CCU 204. A plate-like hole is formed on the front surface of the CCU 204 and a flat metallic ring-like outer fitting frame (plug shell) 209a of the electrical receptacle 209 with which the electrical plug 202 can be connected is fitted in the hole to the metallic CCU frame 204a with screws.

An insulator 231 provided with a flat ring-like containing part in which the base 211 of the electrical plug 202 can be contained is fitted within the outer fitting frame 209a. A plurality of electrical contacts 232 are fitted to the deep side within this insulator 231. The respective electrical contacts 232 are connected with a signal processing circuit (not illustrated) through signal lines.

A hygroscopic member 235 is fitted through a metallic hygroscopic member receiving member 234 fitted to this outer fitting frame 209a with screws 233 near the inlet of the electrical receptacle 209 to act as a proximal end of the outer fitting frame 209a. The outer peripheral side of such elastic member having a hygroscopic function as of a sponge made ring-like is contained by pressing within a recess or groove provided on the inner wall surface of the flat ring-like hygroscopic member receiving member 234 and the inner peripheral side of this hygroscopic member 235 projects inside.

When the base 211 part of the electrical plug 202 is inserted into the plug connecting containing part of the electrical receptacle 209 provided with the hygroscopic member 235, the tip side projecting inside the hygroscopic member 235 will be pressed, thereby providing contact with the flat surface of the base 211. Therefore, when the operation to be inserted into the deep side of the containing part is made, even if a moisture 236 (See FIG. 7A) is deposited on the surface of the base 211, the moisture 236 will be absorbed in the case of contact with the hygroscopic member 235 and will be removed from the surface of the base 211.

Figure 7B:
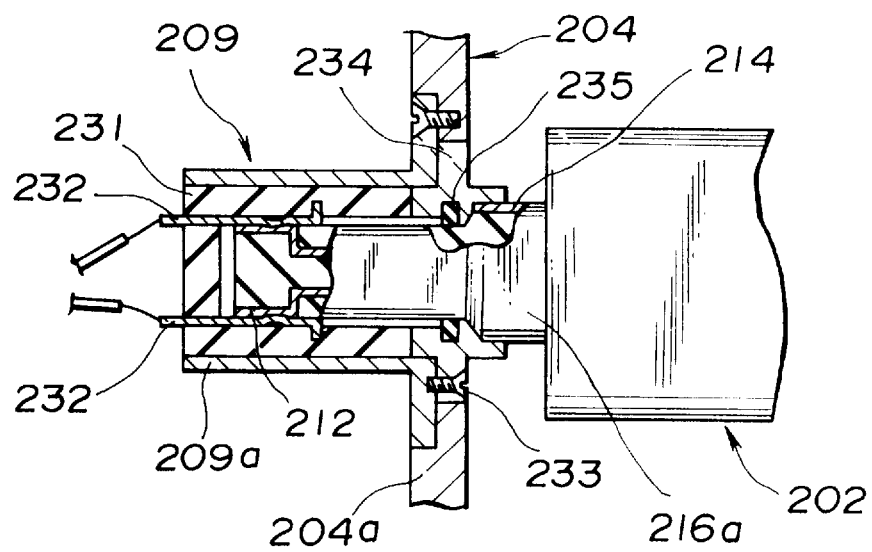

As shown in FIG. 7B, when the electrical plug 202 is fitted to the electrical receptacle 209, the contact patterns 212 exposed on the surface on the tip side of the base 211 will contact the respective electrical contacts 232 of the electrical receptacle 209.

Therefore, the CCU 204 and TV camera 203 will be electrically connected with each other. In this fitted state, the shielding pattern 214 of the thick part 216a will contact the projected part of the hygroscopic member receiving member 234. Therefore, this shielding pattern 214 will conduct with the outer fitting frame 209a through the hygroscopic member receiving member 234 and will keep the shielding function.

According to this embodiment, fitting of the electrical plug 202 to the electrical receptacle 209 results in removal of the moisture remaining on the surface of the base 211 of the electrical plug 202 by the hygroscopic member 235 and a short-circuit can be prevented.

When the hygroscopic member 235 is wet, it may be taken out of the recess of the hygroscopic member receiving member 234 and may be replaced with a new hygroscopic member or another dried hygroscopic member or may be replaced with a new hygroscopic member including the hygroscopic member receiving member 234 by the screws 233.

In this first embodiment, with the electrical plug 202, as the plurality of contact patterns are formed in parallel in the direction (that is, like belts on the rear end side from the tip) of inserting the contact patterns 212 into the electrical receptacle 209, even if the electrical plug 202 is mistakenly removed from the electrical receptacle 209, for example, when the power source of the CCU 204 is on, the respective contact patterns 212 will not conduct from the electrical contacts 232 which have been conducting and will not conduct with electrical contacts other than the GND (that is to say, no mis-connection will occur) and a failure will be effectively prevented.

Figure 8:
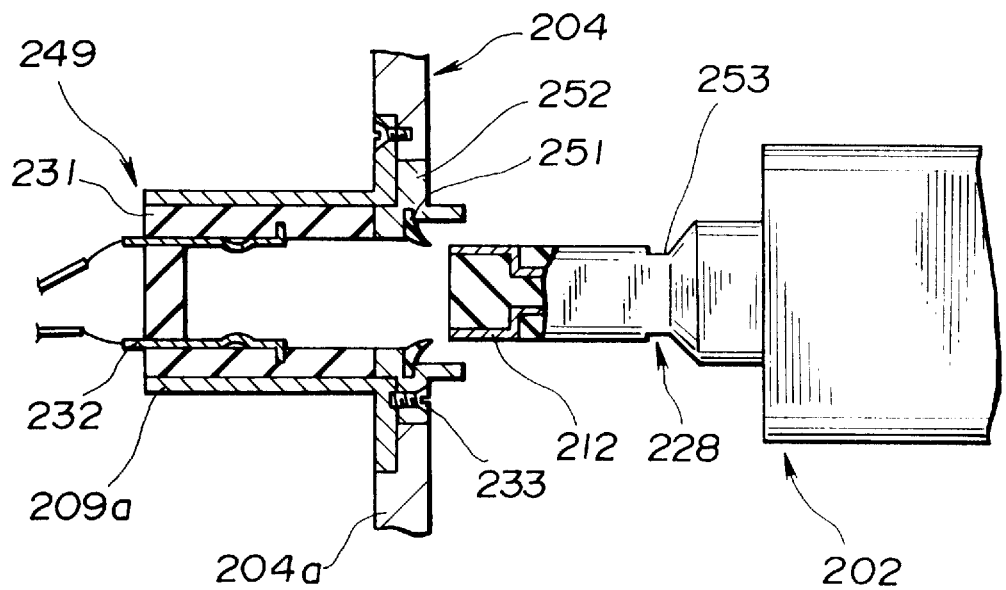
FIG. 8 is a sectioned view showing the peripheral structure of the electrical receptacle in the second embodiment of the present invention.

FIG. 8 shows the periphery of the electrical receptacle 249 in the second embodiment. In this second embodiment, instead of the hygroscopic member 235 in FIG. 7A, a wiper 251 for wiping off liquid moisture is fitted through a wiper receiving member 252. The tip of wiper 251 may closely contact the base surface of the electrical plug 202 and the liquid wiped off may be collected in a receiving groove 253 on the rear side of the base of the electrical plug 202. Because this receiving groove 253 is in an insulating member part on the rear side of the exposed part of the contact pattern 212, a short-circuit cannot occur. The electrical plug 202 and the others are of the same formation as in the first embodiment. The groove for collecting the liquid wiped off may be provided on the electrical receptacle 249 side.

Figure 9:
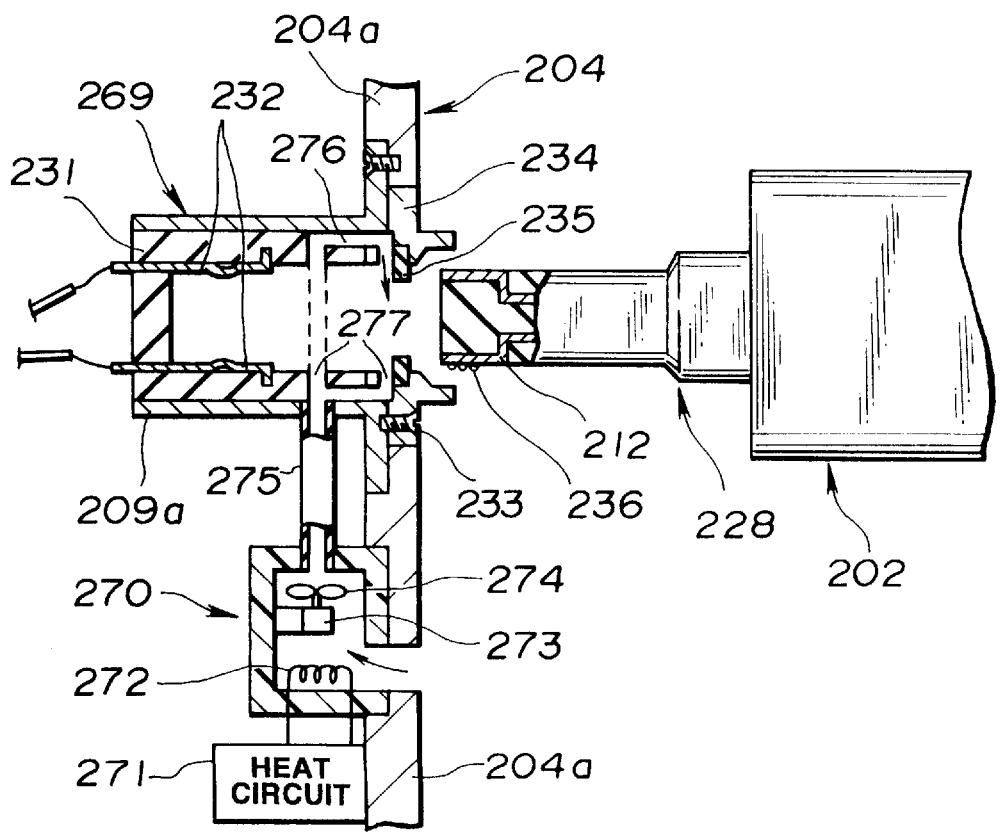
FIG. 9 is a sectioned view showing the peripheral structure of the electrical receptacle in the first modification of the second embodiment.

FIG. 9 shows the structure of the periphery of the electrical receptacle 269 in the first modification of the second embodiment.

In this modification, for example, in FIG. 7A, further, an air feeding mechanism 270 is provided to dry the hygroscopic member 235 and the inserted electrical plug 202.

A chamber opening out is provided below the electrical receptacle 269. An electrical heating wire 272 connected to a heating circuit 271 is contained in the chamber. The air heated by this electrical heating wire 272 is delivered from an opening 277 on the inner wall surface of an insulator 231 to the inside of this inner wall surface through a tube 275 connected to an opening provided above and through a path 276 within the insulator 231 connected with this tube 275 by a fan 274 fitted to a motor 273.

The opening 277 is provided near a hygroscopic member 235 provided near the inlet to evaporate and dry the liquid of the hygroscopic member 235 and to evaporate the liquid of the electrical plug 202 inserted into the electrical receptacle 269.

According to this modification, even if the hygroscopic member 235 is wet, it will be dried within a short time by heated air. Therefore, even if the hygroscopic member 235 is not often replaced, the function of removing liquid from the electrical plug 202 will be able to be retained. In this modification, heated air is used for drying but air not heated may also be used.

Also, an air feeding mechanism may be provided for the second embodiment in FIG. 8.

Figure 10:
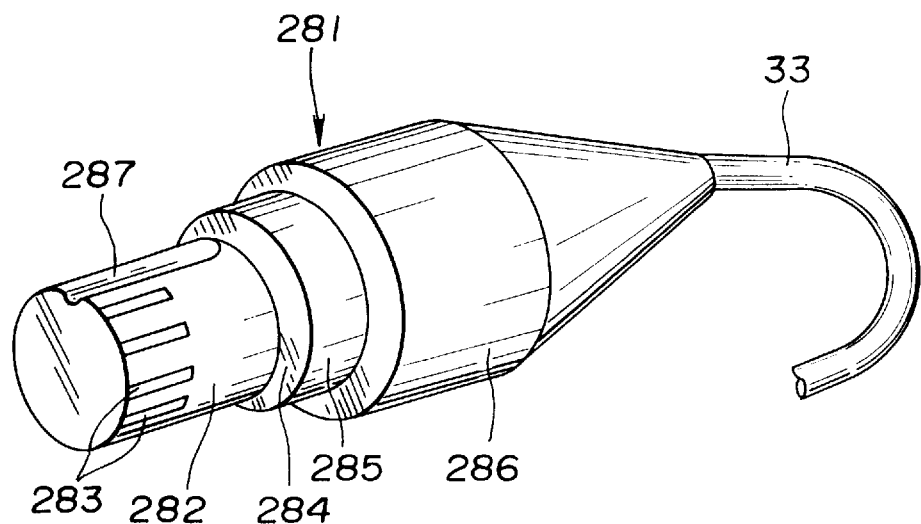
FIG. 10 is a perspective view showing the contour of an electrical plug in the third embodiment.

FIG. 10 shows an electrical plug 281 in the third embodiment. Whereas the electrical plug 202 of the first or second embodiment is like a flat plate as shown in FIG. 6A, the electrical plug 281 of this embodiment is columnar. That is to say, a plurality of contact patterns 283 are provided so as to be exposed on the tip side surface of a base 282 formed of a columnar insulating member.

The exposed contact patterns 283 are flush with the columnar outer peripheral surface of the base 282. A ring-like shielding pattern 285 is formed in the rear large diameter part 284. A cover 286 is provided in the rear of this shielding pattern 285.

For positioning, for example, an incision 287 is provided in one place on the outer peripheral surface of the base 282 and a projection is provided in a position corresponding to this incision 287 on the electrical receptacle side (not illustrated) provided with a columnar containing part with which this electrical plug 281 can be connected so that the electrical plug and electrical receptacle may not be connected with each other unless the incision 287 is positioned on the projection. The others are the same as in the first embodiment.

Figure 16:
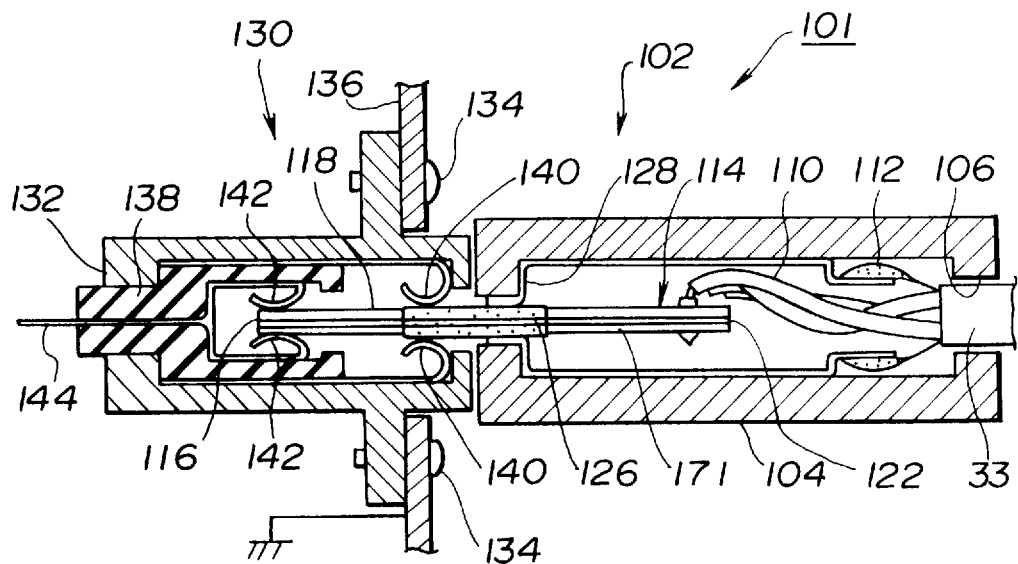

An electrical connector 101 of the fourth embodiment of the present invention shall be explained in the following. As shown in FIG. 16, the electrical connector 101 of the fourth embodiment comprises an electrical plug 102 provided at the distal end of a cable 33 and an electrical receptacle 130 provided, for example, in a CCU and having an opening or recess with which this electrical plug 102 can be removably connected.

Figure 11:
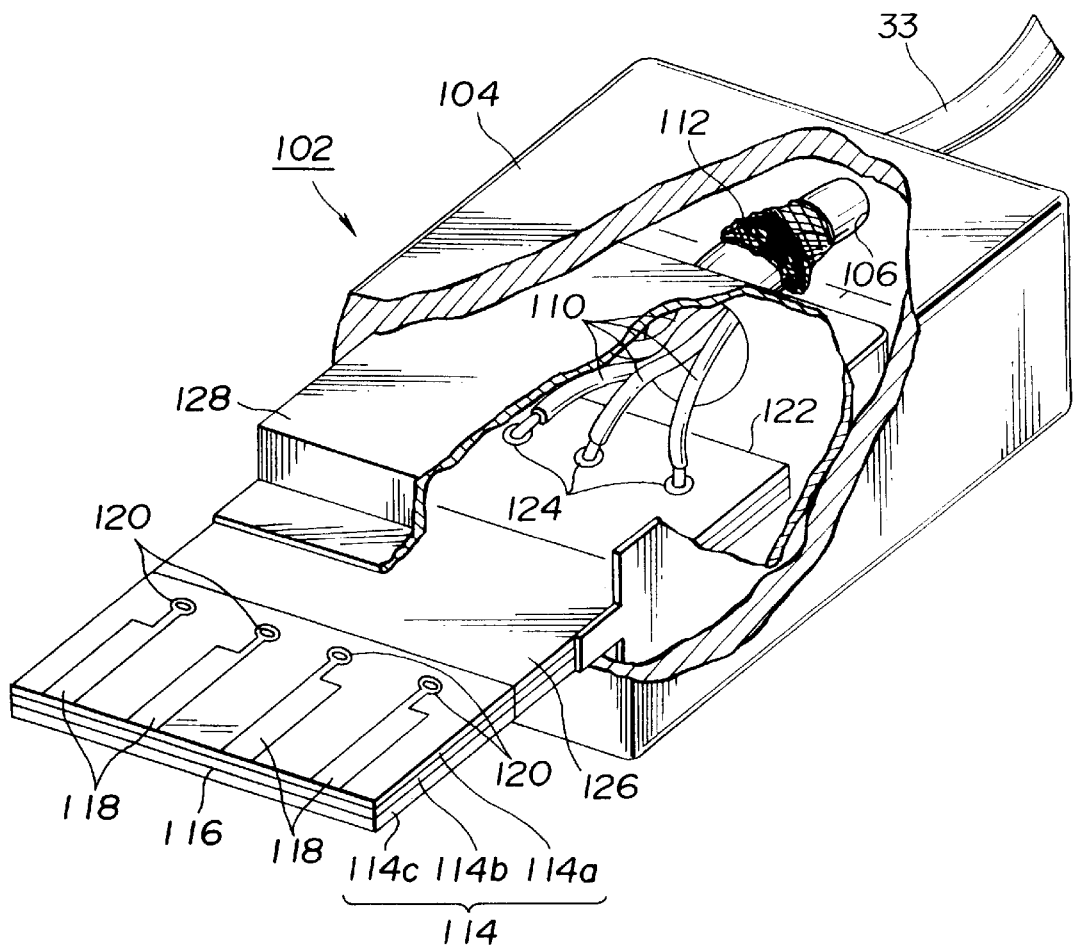
FIGS. 11 to 16 relate to the fourth embodiment of the present invention.

FIG. 11 illustrates the plug 102 having a plug case 104 formed of an insulator. A through-hole 106 is formed in the rear wall of this plug 102 and the cable 33 passes through this through-hole 106. For example, four core wires 110 and a general shield 112 covering these core wires 110 pass inside the jacket of this cable.

An opening is formed in the front wall of the plug case 104. A printed wiring board 114 is arranged halfway within the case through this opening. Circuits electrically connecting the core wires 110 of the cable 33 with the electrical contacts 118 by the printed patterns of this printed wiring board 114 are formed.

That is to say, in this printed wiring board 114, four electrical contacts 118 are formed of printed wirings at one end (called an inserting side end or distal end and represented by a reference numeral 116) becoming a tip projecting from the plug case 104. These electrical contacts 118 are formed like belts in a direction in parallel with the inserting direction (that is, as directed to the proximal end side from the distal end) and are respectively electrically connected to four first through-holes 120 by respective thin linear patterns from the rear end.

Four second through-holes 124 are formed at the other end (which shall be called the cable side end or rear end and represented by a reference numeral 122 hereinafter) on the side opposed to the inserting side end 116 of the printed wiring board 114. The core wires 110 of the cable 33 are respectively soldered to these second through-holes 124.

Between the first through-holes 120 and second through-holes 124, an electromagnetically shielding pattern 126 is formed of printed wirings over the entire periphery in the width direction (that is, the horizontal direction intersecting at right angles with the inserting direction) of the printed wiring board 114. Particularly, the electromagnetic shielding pattern 126 is formed of electrical conductors in a position farther than the electrical contacts 118 as seen from the inserting side end 116 of the printed wiring board 114, that is, from the rear side.

This electromagnetic shielding pattern 126 is arranged so as to be half-way exposed, for example, from the plug case 104 and is in electrical contact with a shielding member 128 arranged within the plug case 104. This shielding member 128 is formed of a copper plate or the like and has the general shield 112 of the cable 33 electrically connected to its rear wall.

Thus, the plug case 104 substantially covers the components of the plug 102 but only the half of the inserting side end 116 side where the electrical contacts 118 of the printed wiring board 114 are provided and the cable 33 are exposed.

Figure 12:
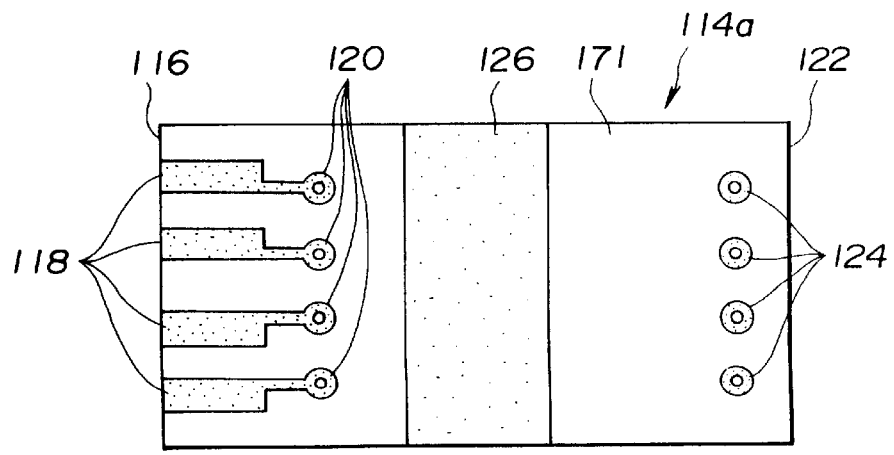
Figure 13:
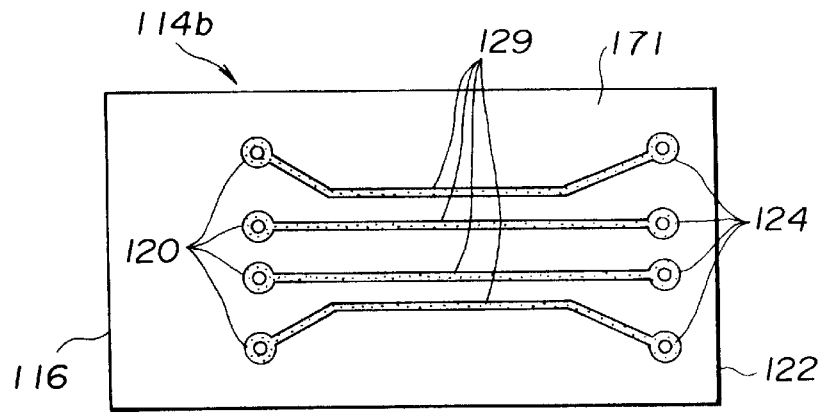
Figure 14:
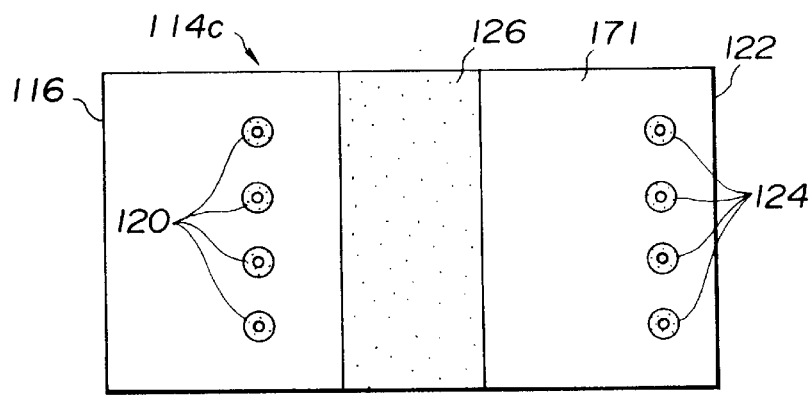

The printed wiring board 114 has a structure including three layers as is shown in FIGS. 12 to 14. On the upper surface of the printed wiring board 114a of the first layer shown in FIG. 12, the electrical contacts 118, the first and second through-holes 120 and 124 and the electromagnetic shield pattern 126 are formed.

On the upper surface of the printed wiring board 114 of the second layer shown in FIG. 13, wirings 129 electrically connecting the first and second through-holes 120 and 124 with each other are formed. On the lower surface of the printed wiring board 114c of the third layer shown in FIG. 4, the first and second through-holes 120 and 124 and the electromagnetic shielding pattern 126 are formed. In the printed wiring board 114i (i=a, b, c) of each layer, the electrical contacts 118, through-holes 120 and others shown in FIGS. 12 to 14 are formed by etching of such insulating substrate 171 as a bakelite, glass epoxy or paper epoxy substrate on which a printed wiring copper foil or the like is formed.

When the plug 102 is thus formed, the electrical contacts 118 and the like of the plug 102 will be able to be made by substantially the same method as the ordinary printed wiring producing process to provide high density. Further, when three layers of the insulating substrate 171 are used, the strength of the plug inserting part which is inserted and pulled out will increase, the durability will improve, the existing print wiring members will be able to be used to form the plugs and, therefore, the cost will be able to be reduced.

The above-described receptacle 130 to receive the plug 102 has a receptacle case 132 formed of an electrical conductive member having a shielding function as shown in FIG. 16. This receptacle case 132 is fixed to the inside surface of a housing 136 of such signal processing apparatus as a CCU and has a plug inserting opening (or recess) corresponding to the opening of the housing 136.

This housing 136 is formed of such conductor as a copper plate or aluminum plate and the receptacle case 132 is earthed through this housing 136. A contact member case 138 made of an insulator is arranged at the end opposed to the plug inserting opening, that is, in the inner part of the opening. This contact member case 138 has a volume, for example, about half that of the receptacle case 132.

The proximal end part of an electromagnetic shielding contact member 140 is inserted between the receptacle case 132 and contact member case 138. The tip part of this contact member 140 extends out to the front of the plug inserting opening.

Figure 15:
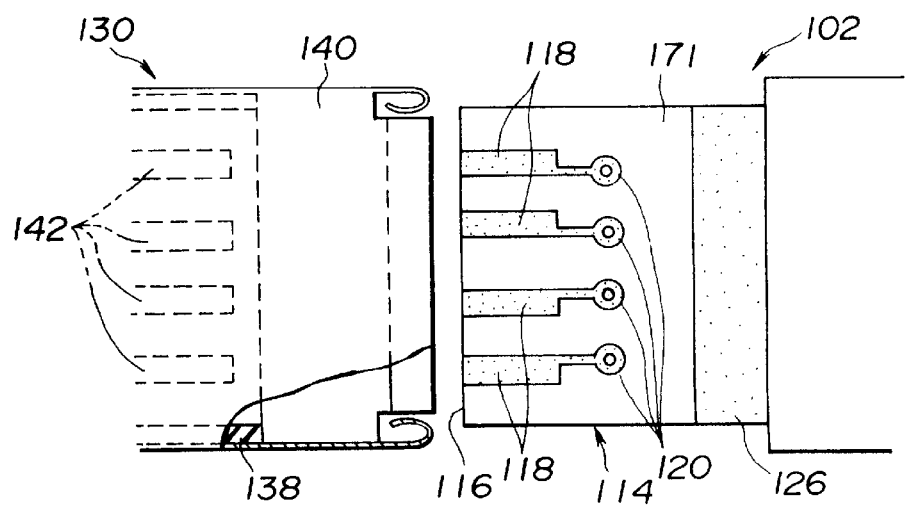

FIG. 15 shows the vicinity of the inserting opening of the receptacle 130 as the receptacle case 132 is removed and the distal end side of the plug 102 to be fitted to and removed from the receptacle 130. In the electromagnetic shielding contact member 140, the end side of a tubular conductor larger than the size of the distal end side of the plug 102 is bent inward vertically and horizontally to form a contact part 140a to contact the respective vertical and horizontal surfaces of the shielding pattern 126.

Therefore, in the case where the plug 102 is inserted into the receptacle 130, as shown in FIG. 16, the electromagnetic shielding contact member 140 will contact the entire periphery, that is, all the respective vertical and horizontal surfaces of the electromagnetic shielding pattern 126 of the printed wiring board 114 and a sufficient shield will be made.

The electrical contact member 142 is secured to the inside surface of the recess of the contact case 138. When the plug 102 is inserted into the receptacle 130 as shown in FIG. 16, the tip of this electrical contact member 142 will contact the electrical contacts 118 of the printed wiring board 114. The proximal ends of these electrical contact members 142 extend outside the receptacle case 132 as enclosed with the proximal end of the contact case 138 and conduct with an external terminal 144 connected to such electrical circuits as a CCD driving circuit of the CCU and video signal processing circuit the same as in FIG. 2.

The operations of the thus formed electric connector 101 of the seventh embodiment shall be explained in the following.

When the plug 102 is inserted into the receptacle 130, the electrical contacts 118 of the printed wiring board 114 will contact the tips of the electrical contact members 142 on the receptacle 130 side. Substantially at the same time, the electromagnetic shielding pattern 126 of the printed wiring board 114 will contact the tip of the electromagnetic shielding contact member 140 on the receptacle 130 side. The wirings 129 leading from the electrical contacts 118 to the shielding members 128 will all be electromagnetically shielding by the electrical contact of the electromagnetic shielding patterns 126 and contact members 140 with the receptacle case 132 and housing 136 formed of conductors.

That is to say, as understood from FIG. 16, the electrical contacts 118 (and wirings 129) among the parts projecting out of the plug 102 will be electromagnetically shielded by the electromagnetic shielding contacts members 140 and electromagnetic shielding patterns 126. The proximal end side of the plug 102 will also be shielded in the structure.

In the case where the plug is connected to the receptacle, the electrical contacts and the like projecting out of the plug will most likely provide insufficient shielding. In this embodiment, no member formed specially independently to electromagnetically shield the plug 102 is provided but the electromagnetic shielding patterns 126 are formed on the printed wiring board 114 and the electromagnetic shielding contact members 140 conducting to the electromagnetic shielding pattern 126 are provided on the receptacle 130 side so that, in the case where the plug 102 is connected to the receptacle 130, a sufficient electromagnetic shielding function may be obtained.

Also, in this embodiment, the electrical contacts 118 of the plug 102 are formed parallel to one another so as to be belt-like in the inserting direction and the receptacle 130 side electrical contact members 142 functioning as receiving contacts are respectively formed in the positions opposed to the electrical contacts 118 on the deep side of the recess.

Therefore, in the case where the distal end side of the plug 102 is inserted into the receptacle 130 side, except where the electrical contacts 118 provided at the distal end 116 of the plug 102 contact the shielding contact members 140 during insertion, the electrical contacts 118 will contact the electrical contact members 142 as the corresponding receiving contacts but will not conduct with any other receiving contacts.

After use, while the plug 102 is being moved to the rear side to be removed from the receptacle 130, the electrical contacts 118 will likely contact the shielding contact members 140 but will not conduct with any other receiving contacts.

Therefore, when the power source of such an apparatus as a CCU to which the receptacle 130 is connected is mistakenly turned on, even if the plug 102 is removed from the receptacle 130, a failure will be able to be prevented.

By the way, the method of fixing the core wire 110 to the printed wiring board 114, fixing the shielding member 128 to the electromagnetic shielding pattern 126 or fixing the general shield 112 to the shielding member 128 is not limited to soldering but may consist of pressing the member, for example, with a screw.

Figure 17:
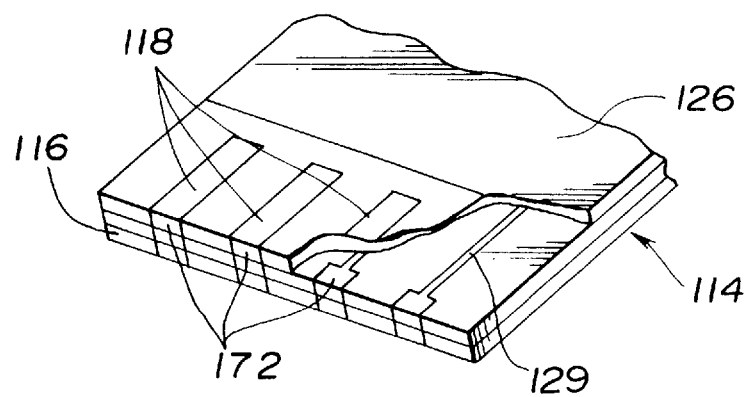
FIG. 17 is a perspective view showing a summary of the internal structure of the plug in the modification of the fourth embodiment.

Also, the method of conducting the electrical contacts 118 of the printed wiring board 114a of the first layer of the printed wiring board 114 to the wirings 129 of the printed wiring board 114b of the second layer is not limited to be by the through-holes 120 but, as shown, for example, in FIG. 17, the electrical contacts 118 may be extended out to the positions corresponding to the wirings 129 on the surface of the printed wiring board 114b of the second layer from the surface of the printed wiring board 114a of the first layer through the conducting patterns 172 provided on the end surface of the inserting side end 116 of the printed wiring board 114.

Also, it is evident that this conducting means may be provided at the cable side end 122.

Figure 18:
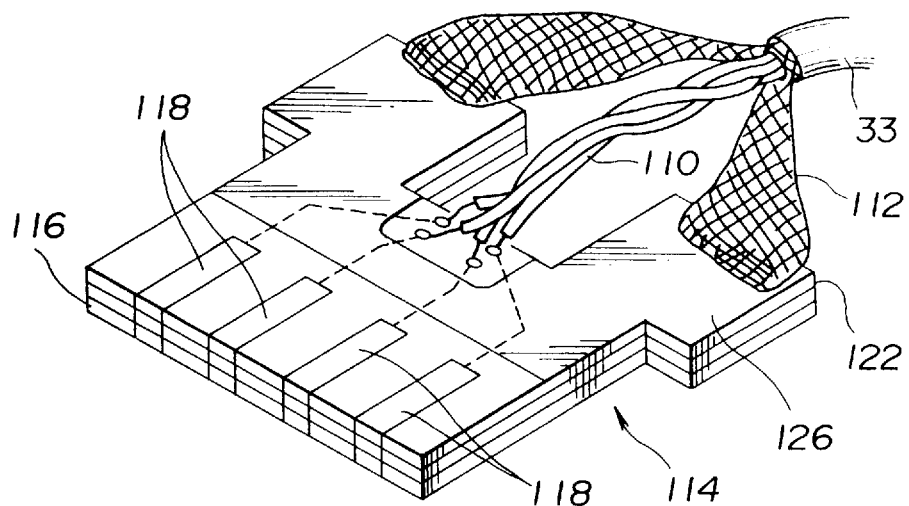
FIG. 18 is a perspective view showing a printed wiring board in the modification of the fourth embodiment.

Further, in the plug 102, without using the shielding member 128, as shown in FIG. 18, a general shield 112 may be soldered to the rear end side of the electromagnetic shielding pattern 126. Thus, the shielding member 128 will become unnecessary, the assembly will be made simple and the cost will be able to be reduced.

The fifth embodiment of the present invention shall be explained in the following. In the fourth embodiment, in the case where the plug 102 is fitted to or removed from the receptacle, the plug side electrical contacts 118 will contact the receptacle side electromagnetic shielding contact members 140. In the case where the plug 102 is connected with the image taking device, the electrical contacts 118 will not be influenced by static electricity when they conduct with the shield potential or GND more than when they are released and, therefore, there will be few problems.

However, in the case of fitting and removing the plug, it may be preferable that they are released. Also, as described in the later embodiment, the electrical contacts 118 are likely to be deteriorated by sliding.

Therefore, in this embodiment, the electrical contacts will be prevented from contacting the receptacle side electromagnetic shielding contact members even in the case of fitting and removing the plug.

Figure 19:
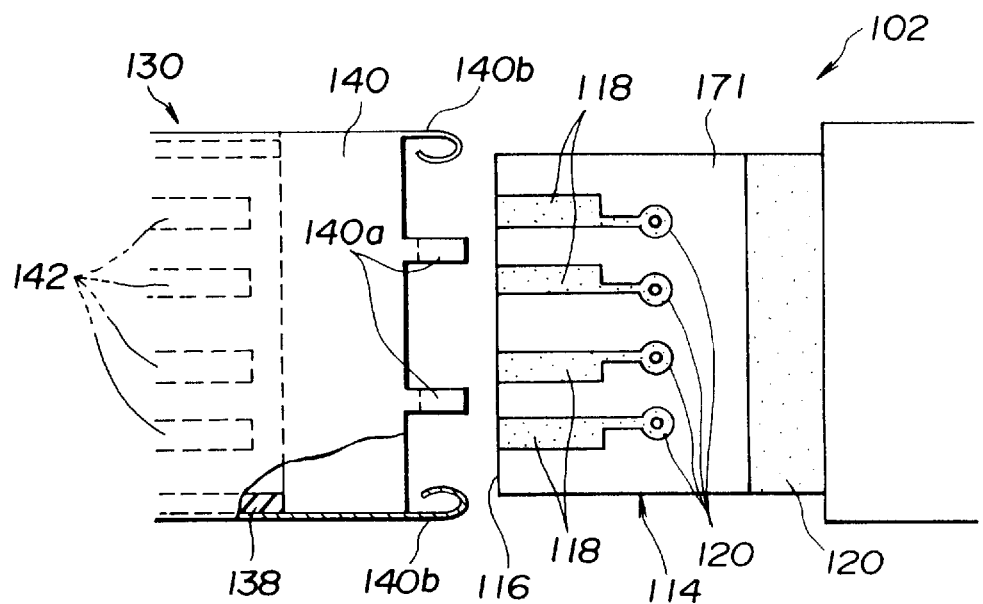
FIG. 19 is a plan view showing an arrangement of the contact parts of the electromagnetic shielding contact members and the electrical contacts in the fifth embodiment.

In this embodiment, the shielding contact members 140 are provided as shown in FIG. 19 in which, the same as in FIG. 15, the receptacle 130 as the shielding case 132 is removed is shown in a plan view.

That is to say, the contact parts (represented by the reference numeral 140a in FIG. 19) at the distal end, for example, in the vertical (or thickness) direction of the shielding contact member 140 are formed to project on the plug side and in the vertical direction in the positions between the electrical contacts 118 adjacent in the horizontal (or width) direction. According to this formation, when the plug is fitted and removed, the contact parts 140a of the shielding contact member 140 will slide and move on the surface of the insulating member 171 and will contact the shielding contact 126 near the fitted state. In FIG. 19, only the side contact parts (represented by the reference numeral 140b in FIG. 19) may be provided. Also, in FIG. 19, the side contact parts 140b may not be provided.

According to this formation, when the plug is fitted and removed, except in the correctly fitted connection, a disconnection will occur. Therefore, the mis-connection can be positively prevented from occurring and the failure or the like can be effectively prevented from occurring.

By the way, in FIG. 19, the proximal end side of the contact part 140a is constructed like a wide plate so that the others than the contact part 140a may be hard to deform, the contact part 140a may be easy to position and the durability may be improved. The invention is not limited to such a plate-like construction. The number of the contact parts 140a to be provided is not limited to that shown in FIG. 19.

The sixth embodiment of the present invention shall be explained in the following with reference to FIGS. 20A and 20B. By the way, the same members as in the fourth embodiment shall bear the same reference numerals and only the differences shall be explained. Hereinafter, the seventh to twelfth embodiments shall also be explained in the same manner.

Figure 20A:
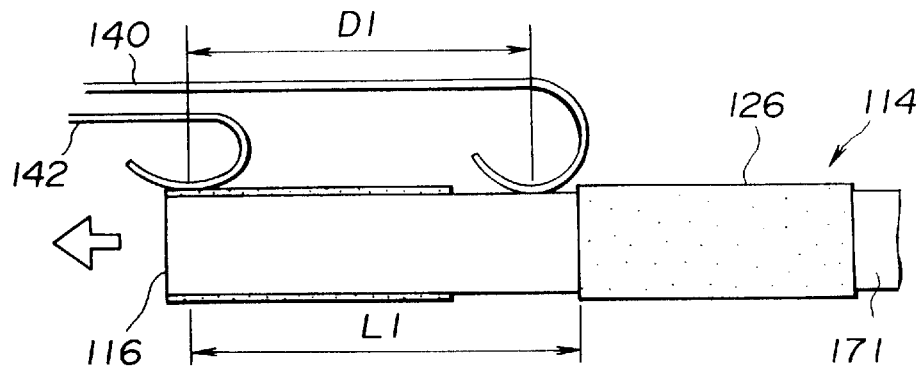
FIGS. 20A and 20B relate to the sixth embodiment of the present invention.

In the formation of the fourth embodiment, as shown in FIG. 20A, when the inserting side end 116 (See FIG. 11) of the printed wiring board 114 is inserted into the plug insertion opening of the receptacle 130 (See FIG. 15), the connection (which shall hereinafter be called the "electrical connection") of the electrical contacts 118 with the electrical contact members 142 will be likely to be made prior to the connection (which shall hereinafter be mentioned as the "shielding connection") of the electromagnetic shielding pattern 126 with the electromagnetic shielding contact member 140. In this formation, when the plug 102 is inserted into and removed from the receptacle 130, the electrical connection will be made when the shielding connection is not made. Therefore, when noises are produced the moment the electrical contact is made, these radiated noises will not be shielded.

Figure 20B:
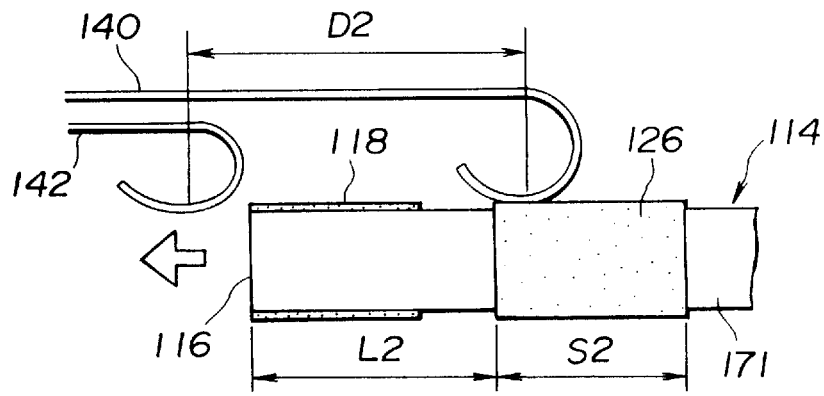

In consideration of such a case, in this embodiment, as shown in FIG. 20B, the contact interval D2 between the receptacle side electromagnetic shielding contact member 140 and the electrical contact member 142 is made larger than the distance L2 from the inserting side end 116 to the tip of the shielding pattern 126 so that the shielding connection, that is, the connection of the electromagnetic shielding pattern 126 with the electromagnetic shielding contact member 140 may be made prior to the electrical contact. That is to say, in FIG. 20B, D2>L2 is set. As shown in FIG. 20A, in the case of the fourth embodiment, if the contact interval is D1 and the distance is L1, D1<L1 will be possible.

Thus, in this embodiment, the shielding connection is always made prior to the electrical connection. Further, even after the electrical connection is made, the shielding connection will be retained. Therefore, when the plug 102 is moved in the direction indicated by the arrow from the state in FIG. 20B and the electrical contact member 142 contacts the electrical contacts 118 and is electrically connected, the shielding contact member 140 will still be kept in contact with the shielding pattern 126.

This meets the condition (S2>D2−L2) that, in the case where the length for which the shielding pattern 126 is provided, that is, the length from its tip to the rear end is S2, at least this length S2 will be greater than D2−L2. Thereby, when the plug is fitted to and removed from the receptacle, the shielding function will not be eliminated and the radiated noises will be reduced.

In the formation of the sixth embodiment, if the electromagnetic shielding contact member 140 and the GND contact are made common to each other, it will be effective, for example, for latching up the CCD.

The seventh embodiment shall be explained in the following with reference to FIG. 21.

In this embodiment, the printed wiring board 114 is formed to be in the shape of a rectangular tube as shown in FIG. 20, the electrical contacts 118 are formed on the inner peripheral surface and the electromagnetic shielding pattern 126 is formed on the outer peripheral surface. On the receptacle side, the electrical contact member and electromagnetic shielding contact member are formed to be contactable respectively with the electrical contacts 118 and electromagnetic shielding pattern 126.

Thereby, the printed wiring board 114 will not be required to be formed to be of more than three layers and the means of conducting layers with each other will not be necessary. Further, if such formation as is shown in FIG. 18 is adopted, the shielding will be more effective than in the case of using the flat plate-like printed wiring board.

Figure 21:
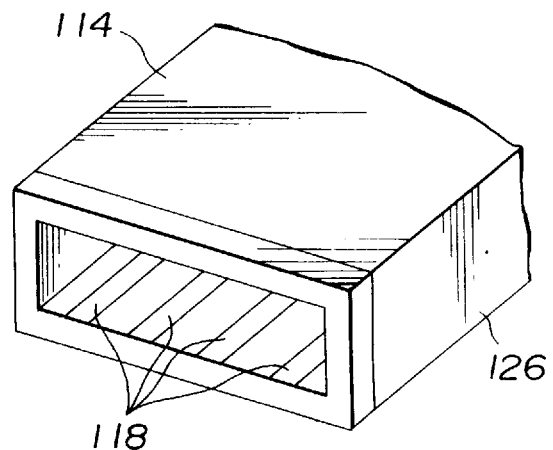
FIG. 21 is a perspective view showing a printed wiring board of the electrical connector in the seventh embodiment.

By the way, the shape of the printed wiring board 114 is not limited to be rectangular tube-like as shown in FIG. 21 but may be polygonal tubular, cylindrical or tubular to attain the effect of this embodiment.

The eighth embodiment shall be explained in the following with reference to FIGS. 22 to 24.

For example, in the fourth embodiment, in the case where the plug 102 is inserted into the receptacle 130, the electrical contacts 118 of the printed wiring board 114 will slide with the contact parts of the shielding contact member 140 on the receptacle 130 side and then will be fitted in contact with the electrical contact member 142.

Also, in the case where the plug 102 is removed from the fitted state, the electrical contacts 118 will be in non-contact with the electrical contact member 142 and then will slide with the contact parts of the shielding contact member 140. As a result, when the plug 102 is repeatedly inserted into and removed from the receptacle 130, the electrical contacts 118 will repeatedly slide with the others than the electrical contact member 142 to be contacted and, therefore, the electrical contacts 118 will be likely to become bad in the contact resulting in a shortened lifetime.

Figure 22:
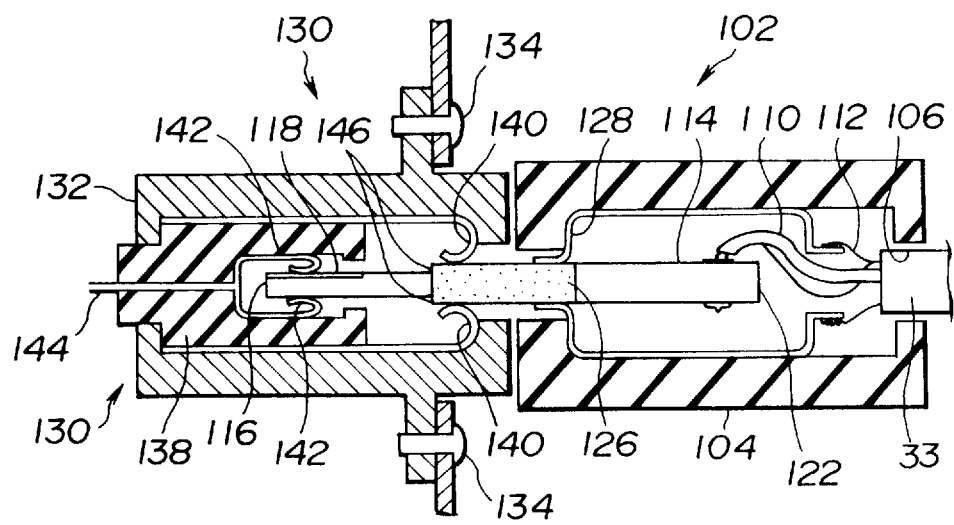
FIG. 22 is a sectioned view showing the electrical connector in the eighth embodiment when the plug is inserted into the receptacle.

Therefore, in this embodiment, as shown in FIG. 22, between the electrical contacts 118 of the printed wiring board 114 and the electromagnetic shielding pattern 126, a level difference 146 in the thickness direction of the printed wiring board 114 is formed and the thickness of the electrical contact 118 and the thickness of the electromagnetic shielding pattern 126 are made different from each other in the thickness direction of the printed wiring board 114.

The interval between the two electrical contact members 142 and the interval between the two electromagnetic shielding contact members 140 are set to be different corresponding respectively to the electrical contacts 118 and electromagnetic shielding pattern 125 different in the thickness.

There are various methods of forming the level difference 146. As shown, for example, in FIGS. 23A and 23B, metal plates 148 jointed closely respectively above and below the electromagnetic shielding pattern 126 are considered. This jointing is made by soldering the metal plate 148 on the end surface to the electromagnetic shielding pattern 126.

Figure 24A:
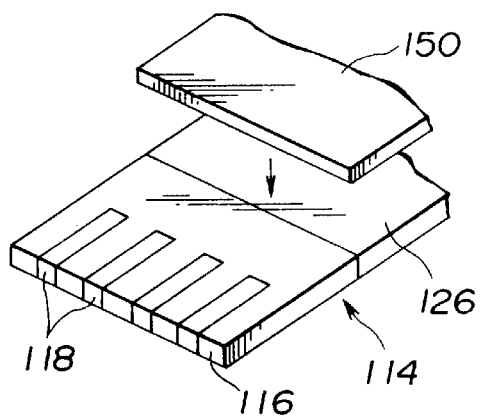
FIGS. 24A and 24B show another example of the method of forming a level difference on the printed wiring board in the eighth embodiment.
Figure 24B:
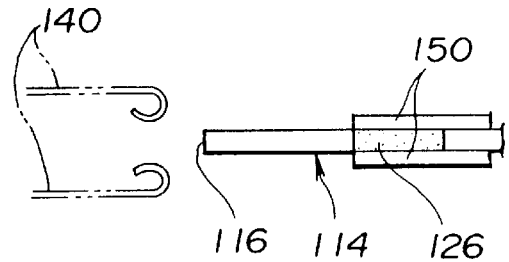

In FIGS. 24A and 24B, instead of the metal plate 148, another printed substrate 150 is closely joined by soldering to the electromagnetic shielding pattern 126 to form the level difference 146. The interval between the contact parts of the opposed shielding contact members 140 is set to be greater than the thickness of the printed wiring board 114 in the parts where the electrical contacts 118 are provided.

When the level difference 146 is thus formed, in the case where the plug 102 is inserted into and removed from the receptacle 130, sliding between the electrical contacts 118 of the printed wiring board 114 and the shielding contact members 140 will be able to be reduced and, therefore, the lifetime of the electrical contacts 118 will be lengthened. Also, the lifetime of the shielding contacts members 140 will also be lengthened as a result of the reduction in the sliding in fitting and removing of the plug.

Figure 23A:
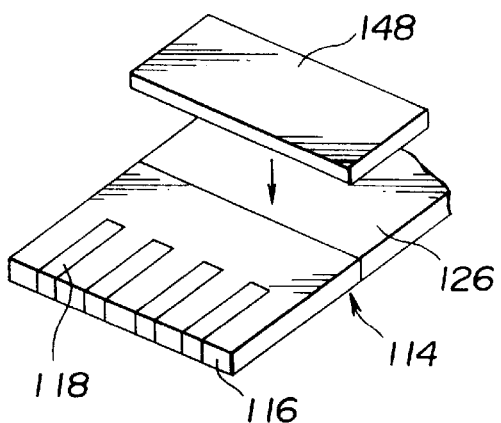
FIGS. 23A and 23B show an example of the method of forming a level difference on the printed wiring board in the eighth embodiment.
Figure 23B:
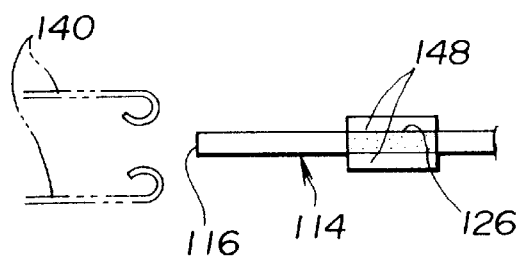

By the way, in FIGS. 23A and 23B, the thickness of the electromagnetic shielding pattern 126 is greater than the thickness of the printed wiring board 114. However, in the printed wiring board 114, stripe-like recesses may be formed in the parts corresponding to the electrical contacts 118 and the electrical contacts 118 may be arranged in these recesses to attain the object of this embodiment.

The ninth embodiment shall be explained in the following with reference to FIGS. 25 and 26.

Figure 25:
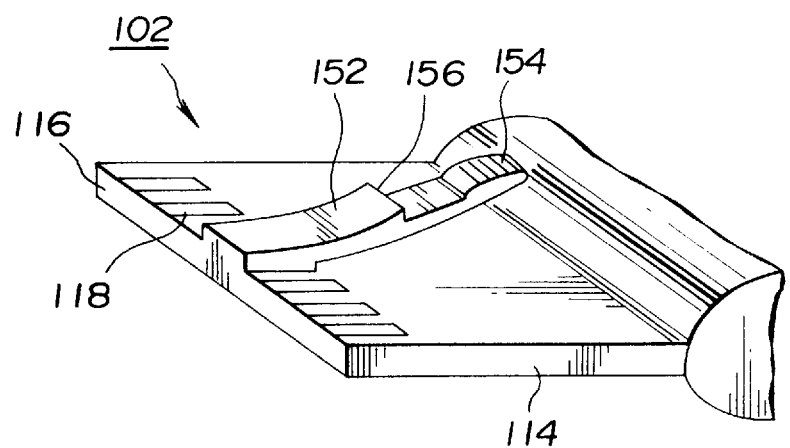
FIG. 25 is a perspective view showing a plug of the electrical connector in the ninth embodiment.

As shown in FIG. 25, a lock arm 152 extends out of the upper surface of the printed wiring board 114 so as to separate away from the inserting side end of the wiring board 114 and to be directed somewhat upward. A releasing part 154 having fine concave-convex streaks formed on the surface to have a large friction coefficient is formed at the tip of this lock arm 152. A locking part 156 having a triangular vertical section is formed in the intermediate part of this lock arm 152.

Figure 26:
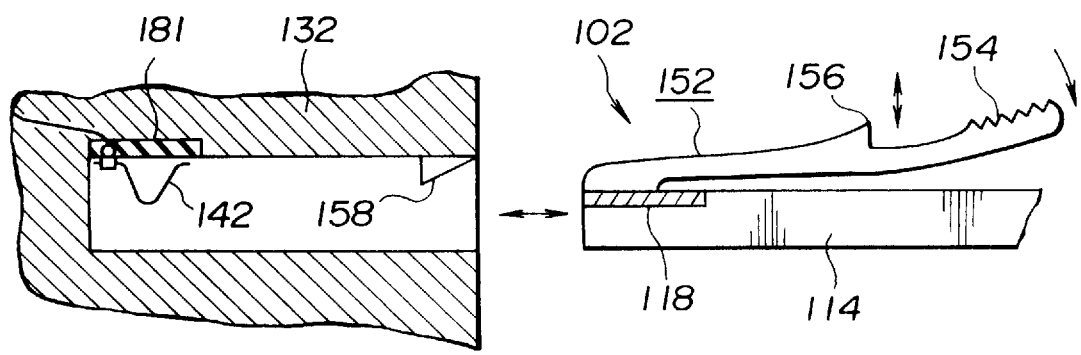
FIG. 26 is a partly sectioned side view showing the plug in FIG. 25 just before it is inserted into the receptacle.

As shown in FIG. 26, an insulating plate 181 is fixed with a receptacle case 132 and electrical contact members 142 are fixed to respective positions contactable with fixed electrical contacts 118 inserted into recesses in this insulating plate 181. A projection 158 to mesh with the locking part 156 is formed near the outlet within this case 132.

When the plug 102 is inserted into the receptacle case 132, the upper surface of the lock arm 152 and the lower surface of the projection 158 will slide on each other and the lock arm 152 will be pushed downward.

When the lock arm 152 is further inserted, the electrical contacts 118 will contact with the electrical contact members 142. When the lock arm 152 is then further inserted until the locking part 156 comes to the projection 158, the locking part 156 and projection 158 will be able to mesh with each other and the locking part 156 will be displaced upward by the energizing force of the lock arm 152 itself and will engage with the projection 158. By this engagement, the plug 102 will be locked with the receptacle case 132. At this time, the releasing part 154 will project out of the receptacle case 132.

When the plug 102 is pulled out of the receptacle case 132, the releasing part 154 projecting out of the receptacle case 132 is pushed down and the engagement, that is, locking of the locking part 156 and projection 158 with each other is released.

By such a simple formation, the plug 102 and receptacle can be positively fitted with each other and a locking mechanism whereby fitting can be easily released can be provided.

Figure 27:
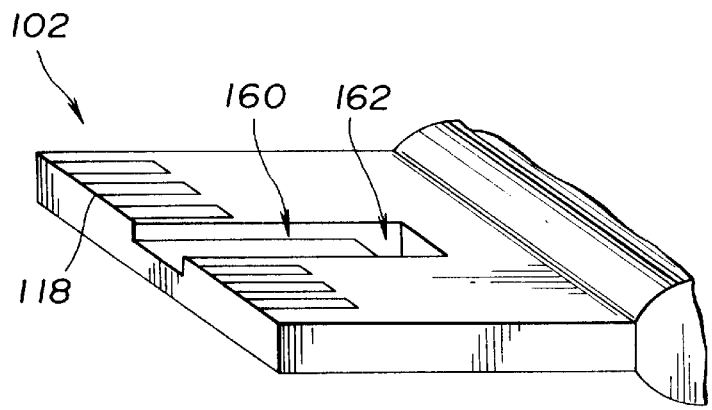
FIG. 27 is a perspective view showing a plug of the electrical connector in the tenth embodiment.
Figure 28:
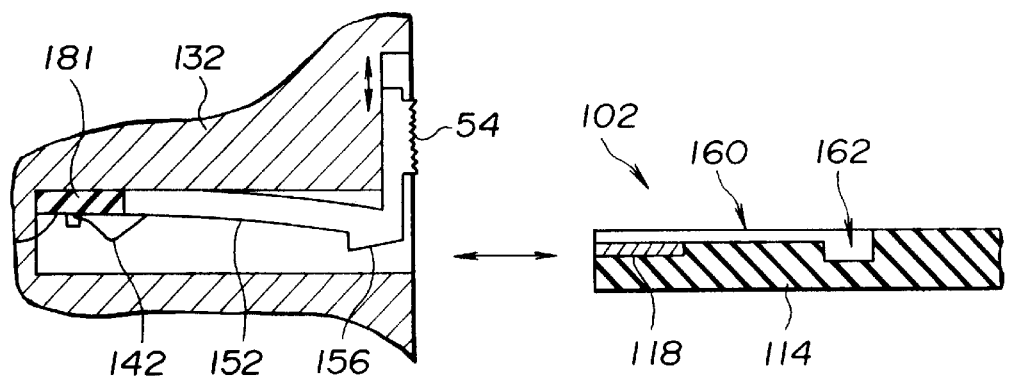
FIG. 28 is a partly sectioned side view showing the plug in FIG. 27 just before it is inserted into the receptacle.

The tenth embodiment shall be explained in the following reference to FIGS. 27 and 28.

In this embodiment, contrary to the ninth embodiment, the lock arm 152 is formed integrally with the receptacle case 132. Particularly, this lock arm 152 is formed in an L-shape having two arm parts. One arm part of the lock arm 152 has a releasing part 154 which is exposed out of the receptacle case 132 so as to be able to be operated by the user. A locking part 156 is formed on the lower surface of the joint part of the two arm parts.

A guide groove 160 extending out in the direction of inserting into and removing from the receptacle case 132 is formed in the printed wiring board 114. A recess 162 having a depth greater than that of the groove 160 and engageable with the locking part 156 is connected with the guide groove 160 at the end.

When the plug 102 is inserted into the receptacle case 132, the locking part 156 of the lock arm 152 will slide on the bottom surface of the guide groove 160 in the printed wiring board 114. When the electrical contacts 118 contact the electrical contact members 142 to be electrically connected, the locking part 156 will engage with the recess 162 and the plug 102 will be locked as fitted to the receptacle case 132.

The other formations, operations and effects of this embodiment are the same as of the ninth embodiment.

The eleventh embodiment shall be explained in the following with reference to FIGS. 29 to 31.

Figure 29:
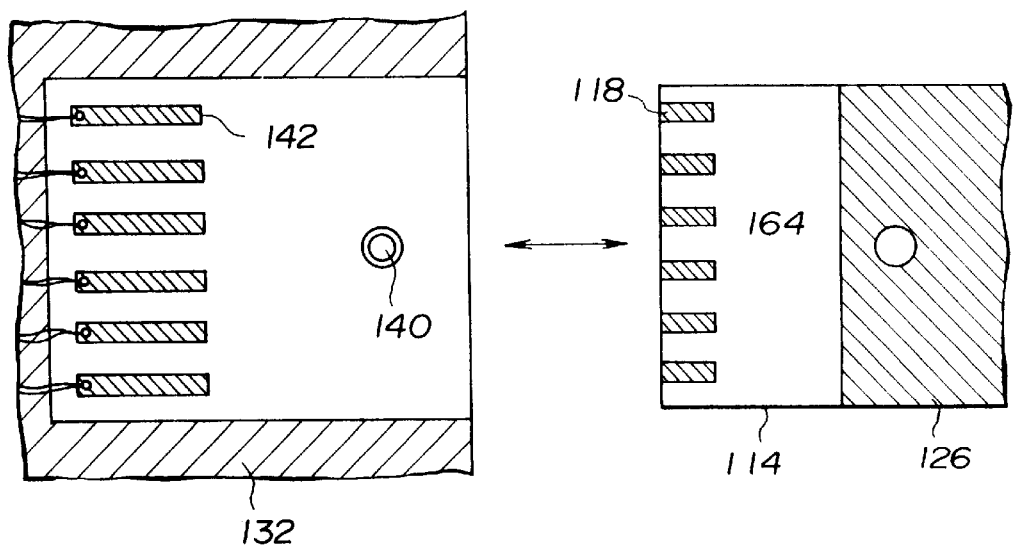
FIG. 29 is a partly sectioned plan view showing the electrical connector in the eleventh embodiment.
Figure 30:
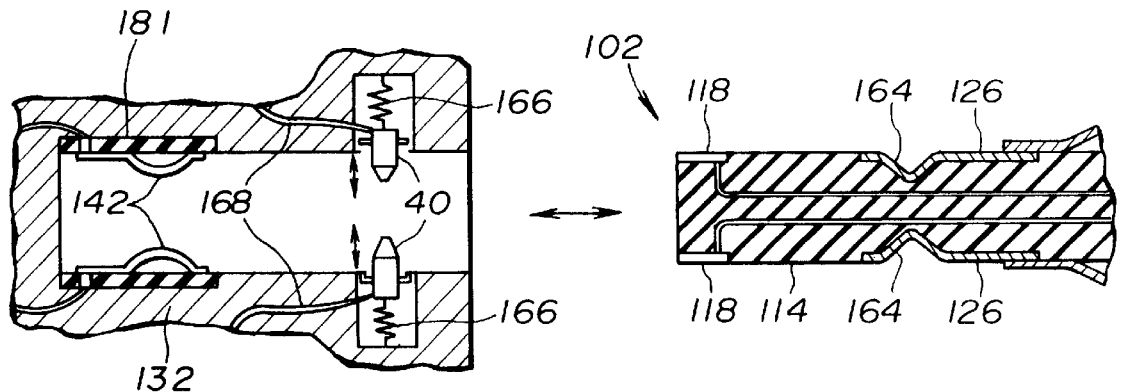
FIG. 30 is a vertically sectioned view of the electrical connector shown in FIG. 29.

In this embodiment, as shown in FIGS. 29 and 30, the electromagnetic shielding patterns 126 are formed to be plates. A locking part 164 consisting of a substantially triangular conical recess is formed on each electromagnetic shielding pattern 126.

An electromagnetic shielding contact member 140 fitted near the plug inserting opening within the receptacle case 132 consists of a short column having a conical shape at the tip. The conical part at the tip of this electromagnetic shielding contact member 140 is engageable with the locking part 164 on the electromagnetic shielding pattern 126.

These electromagnetic shielding patterns 126 are fitted to the receptacle case 132 through resilient members 166 and are pushed against the electromagnetic shielding patterns 126. A shielding wire 168 passing a signal of the electromagnetic shielding pattern 126 to a ground-in (not illustrated) is electrically connected to each electromagnetic shielding contact member 140.

When the printed wiring board 114 is inserted into the receptacle case 132, the conical part at the tip of each electromagnetic shielding contact member 140 will be pushed by the resilient member 166 against the electromagnetic shielding pattern 126, will be engaged with the locking part 162 of the electromagnetic shielding pattern 126 and will be conducted to contact the electromagnetic shielding pattern 126 and then the electrical contact members 142 and electrical contacts 118 will be connected with each other.

Figure 31:
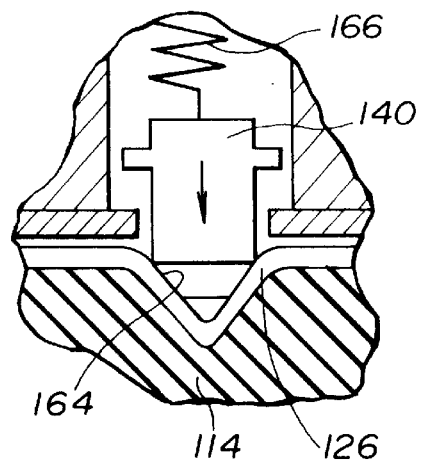
FIG. 31 is a magnified view of the electromagnetically shielding contact shown in FIG. 30.

When the printed wiring board 114 is inserted to a position in which the electromagnetic shielding contact member 140 and locking part 164 coincide with each other, the electromagnetic shielding contact member 140 will be engaged with the locking part 164 by the energizing force of the resilient member 166, as shown in FIG. 31, the printed wiring board 114 will be locked within the receptacle case 132 and a positive conduction to the electromagnetic shielding pattern 126 will be made.

At this time, due to the positive connection of the electromagnetic shielding contact member 140 with the locking part 164, such unnecessary noises as produced by electric waves will be absorbed by the electromagnetic shielding patterns 126 and the electric waves will be able to be passed through the shielding wires 168. As a result, the influence of noise will be eliminated.

Figure 32:
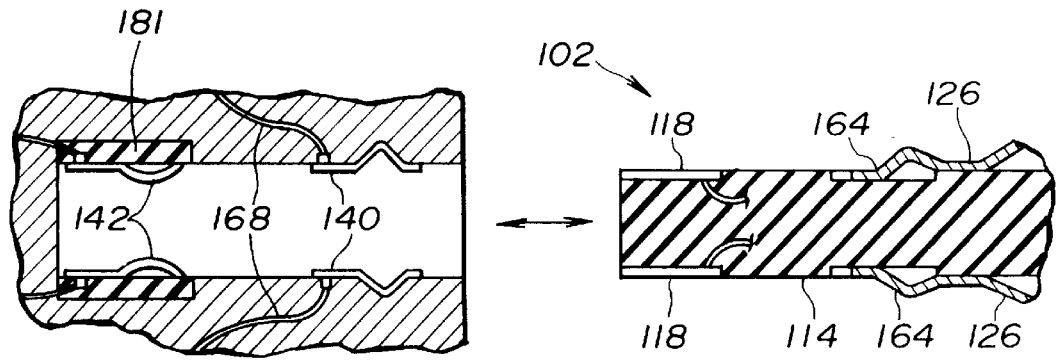
FIG. 32 is a vertically sectioned view showing the electrical connector in the twelfth embodiment.

The twelfth embodiment shall be explained in the following with reference to FIG. 32.

The locking part 164 formed in the electromagnetic shielding pattern 126 is a recess in the tenth embodiment but is a projection out of the printed wiring board 114 in this embodiment. A space is present between this locking part 164 and printed wiring board 114. By the presence of this space, the locking part 164 is transformable within a predetermined range. As a result, the locking part 164 performs a role of a plate spring. The electromagnetic shielding contact member 140 of the receptacle case 132 is recessed to conform to this locking part 164. The other formations are the same as in the eleventh embodiment.

When the printed wiring board 114 of such formation is inserted into the receptacle case 132, the locking part 164 of the electromagnetic shielding pattern 126 will be connected with each electromagnetic shielding contact member 140 by its plate spring function and the conduction of the electromagnetic shielding pattern 126 with the shielding wire will become positive.

The other operations and effects are the same as in the eleventh embodiment. By the way, in this embodiment, each locking part 164 is formed integrally with the electromagnetic shielding contact member 140 but may be separately formed.

Any embodiment formed by partly combining the above-described embodiments also belongs to the present invention.

What is claimed is:

1. An electrical connector comprising:
   an electrical plug having:
      a plate-like substrate having an electrical insulating property;
      a plurality of first electrical contacts which are formed respectively in parallel on at least one side surface at a distal end of said substrate for a predetermined distance from said distal end and joined to conductors embedded within said substrate; and
      a shielding part formed of an electrical conductor to shield and completely surround axial extents of each one of said embedded conductors while leaving unshielded said distal end of said substrate in which said plurality of first electrical contacts are formed; and
   an electrical receptacle having:
      a receiving member forming at least a part of a recess in which said distal end of said substrate is inserted and having an electrical insulating property;
      a plurality of second electrical contacts arranged so as to be fitted to said receiving member in said recess and to contact respectively with said plurality of first electrical contacts whenever said distal end of said substrate is inserted into said recess; and
      at least one shielding electrical contact formed to cover said plurality of second electrical contacts and to contact said shielding part,
      wherein said shielding electrical contact of said electrical receptacle provides a continuous electromagnetic shield which covers all of said plurality of first electrical contacts said plurality of second electrical contacts whenever said electrical plug is mounted to said electrical receptacle such that said shielding electrical contact contacts said shielding part of said electrical plug.

2. An electrical connector according to claim 1 wherein said plurality of first electrical contacts and said shielding part are connected to an electrical cable.

3. An electrical connector according to claim 1 further comprising a shielding case for covering said receiving member around at least said recess with an electrical conductive member and which conducts with said shielding electrical contact.

4. An electrical connector according to claim 1 wherein said shielding electrical contact is formed nearer the opening end of said recess than said second electrical contacts.

5. An electrical connector according to claim 1 wherein said shielding electrical contact is not connected with said first electrical contacts at any stage during insertion or removal of the electrical plug from the electrical receptacle.

6. An electrical connector according to claim 1 wherein, whenever said electrical plug is fitted or removed from said electrical receptacle, said shielding electrical contact is connected with said shielding part before said first electrical contacts are connected with said second electrical contacts.

7. An electrical connector according to claim 1 wherein the vicinity of said shielding part is made thicker than the part in which said first electrical contacts are formed.

8. An electrical connector according to claim 1 wherein, whenever said electrical plug is inserted into said recess to a predetermined position, a locking mechanism regulates the movement in the direction in which said electrical plug is fitted or removed.

9. An electrical connector according to claim 8 wherein a releasing mechanism releases said locking mechanism.

10. An electrical connector according to claim 1 wherein, during insertion of the electrical plug to said electrical receptacle, a plurality of said shielding electrical contacts cover the periphery of an exposed part of said plurality of first electrical contacts.

11. The electrical connected recited in claim 1, wherein said shielding electrical contact includes a liquid removing means for removing liquid from said plurality of first electrical contacts formed in said substrate of said plug whenever said substrate is inserted into said recess.

12. The electrical connector recited in claim 11, wherein said liquid removing means comprises a hygroscopic member fitted to a metallic hygroscopic member receiving member mounted to said shielding contacts, wherein said hygroscopic member contacts said side surface of said substrate when said substrate is inserted into said recess.

13. An electrical connector comprising:
   an electrical plug having:
      an insulating member having an electrical insulating property;
      a plurality of first electrical contacts which are formed respectively in parallel on a surface of said insulating member for a predetermined distance from a distal end of said insulating member and joined to conductors embedded within said substrate; and
      a shielding part formed of an electrical conductor to shield and completely surround axial extents of each one of said embedded conductors while leaving unshielded said distal end of said substrate in which said plurality of first electrical contacts are formed; and
   an electrical receptacle having:
      a receiving member forming at least a part of a recess in which said insulating member is inserted and having an electrical insulating property;
      a plurality of second electrical contacts arranged so as to be formed in said receiving member in said recess and to contact respectively with said plurality of first electrical contacts whenever said insulating member is inserted into said recess; and
      at least one shielding electrical contact formed to cover said plurality of second electrical contacts and to contact said shielding part,
      wherein said shielding electrical contact of said electrical receptacle provides a continuous electromagnetic shield covering the whole of said plurality of first electrical contacts, said plurality of second electrical contacts whenever said electrical plug is mounted to said electrical receptacle such that said shielding electrical contact contacts said shielding part of said electrical plug.

14. An electrical connector according to claim 13 wherein said plurality of first electrical contacts and shielding part are connected to a cable.

15. An electrical connector according to claim 13 further comprising a shielding case for covering said receiving member around at least said recess with an electrical conductive member and which conducts with said shielding electrical contact.

16. An electrical connector according to claim 13 wherein said shielding electrical contact is formed nearer an opening end of said recess than said electrical contacts.

17. An electrical connector according to claim 13 wherein said shielding electrical contact is not connected with said first electrical contacts at any stage during insertion or removal of the electrical plug from said electrical receptacle.

18. An electrical connector according to claim 13 wherein, whenever said electrical plug is fitted to or removed from said electrical receptacle, said shielding electrical receptacle, said shielding electrical contact is connected with said shielding part before said first electrical contacts are connected with said second electrical contacts.

19. An electrical connector according to claim 13 wherein said insulating member is columnar.

20. An electrical connector according to claim 13 wherein said electrical plug is provided in an endoscope and is connected with an image taking device provided with a photoelectrically converting function through a signal cable.

21. The electrical connected recited in claim 13, wherein said shielding electrical contact includes a liquid removing means for removing liquid from said plurality of first electrical contacts formed in said substrate of said plug whenever said substrate is inserted into said recess.

22. The electrical connector recited in claim 21, wherein said liquid removing means comprises a hygroscopic member fitted to a metallic hygroscopic member receiving member mounted to said shielding contact, wherein said hygroscopic member contacts said side surface of said substrate when said substrate is inserted into said recess.

* * * * *